US012594165B2

(12) United States Patent
Knueppel et al.

(10) Patent No.: US 12,594,165 B2
(45) Date of Patent: Apr. 7, 2026

(54) EXPANDABLE MEDICAL IMPLANT FOR ADOLESCENT CRANIUM DEFECTS

(71) Applicant: DePuy Synthes Products, Inc., Raynham, MA (US)

(72) Inventors: Stefan Knueppel, Binningen (CH); Robert Schoutens, Basel (CH); Steffan Daniel, Solothurn (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/331,684

(22) Filed: May 27, 2021

(65) Prior Publication Data

US 2021/0369460 A1      Dec. 2, 2021

Related U.S. Application Data

(60) Provisional application No. 63/030,482, filed on May 27, 2020.

(51) Int. Cl.
A61F 2/28          (2006.01)
A61F 2/30          (2006.01)

(52) U.S. Cl.
CPC .. A61F 2/2875 (2013.01); *A61F 2002/30579* (2013.01); *A61F 2002/30706* (2013.01)

(58) Field of Classification Search
CPC .......... A61F 2/2875; A61F 2002/30579; A61F 2002/30706; A61F 2002/30116; A61F 2002/30143; A61F 2002/30383; A61F 2002/30387; A61F 2002/3039; A61F 2002/30398; A61F 2002/304; A61F 2002/30401; A61F 2002/30428; A61F 2002/30433; A61F 2002/30476; A61F 2002/30484; A61F 2002/30492; A61F 2002/305; A61F 2002/30505; A61F 2002/30518; A61F 2002/30528; A61F 2002/30565; A61F 2002/30571; A61F 2002/30601; A61F 2002/30772; A61F 2002/30777; A61F 2002/30784; A61B 2017/00991; A61B 2017/681; A61B 17/58; A61B 17/68; A61B 17/688; A61B 17/80; A61B 17/8023; A61B 17/8061
See application file for complete search history.

(56) References Cited

U.S. PATENT DOCUMENTS

| | | | | |
|---|---|---|---|---|
| 5,201,737 A | * | 4/1993 | Leibinger | .......... A61B 17/8085 606/280 |
| 5,468,242 A | * | 11/1995 | Reisberg | ............ A61B 17/8085 606/151 |
| 5,578,036 A | * | 11/1996 | Stone | ................. A61B 17/8085 606/281 |

(Continued)

FOREIGN PATENT DOCUMENTS

| | | |
|---|---|---|
| CN | 110801314 A | 2/2020 |
| WO | 2007/050276 A2 | 5/2007 |
| WO | 2016/024248 A1 | 2/2016 |

*Primary Examiner* — Sarah W Aleman
*Assistant Examiner* — Melissa A Hoban
(74) *Attorney, Agent, or Firm* — BakerHostetler

(57) ABSTRACT

The present disclosure is directed to an expandable medical implant for the repair of cranium defects in adolescent patients. The implants of the present disclosure can include a plurality of interconnected links that are movable with respect to each other as the underlying cranium grows and expands.

10 Claims, 19 Drawing Sheets

(56)         References Cited

U.S. PATENT DOCUMENTS

| | | | | |
|---|---|---|---|---|
| 5,766,176 | A * | 6/1998 | Duncan | A61B 17/8085 |
| | | | | 606/281 |
| 5,993,448 | A * | 11/1999 | Remmler | A61B 17/68 |
| | | | | 606/53 |
| 6,159,244 | A * | 12/2000 | Suddaby | A61F 2/4611 |
| | | | | 606/247 |
| 8,298,292 | B2 * | 10/2012 | Swords | A61F 2/30965 |
| | | | | 623/23.72 |
| 8,858,639 | B2 * | 10/2014 | Tigno, Jr. | A61F 2/2875 |
| | | | | 623/17.17 |
| 2006/0235398 | A1 | 10/2006 | Farris et al. | |
| 2007/0293865 | A1 * | 12/2007 | Ko | A61B 17/688 |
| | | | | 606/916 |
| 2008/0200954 | A1 * | 8/2008 | Tucci | A61B 17/688 |
| | | | | 606/151 |
| 2010/0228291 | A1 | 9/2010 | Butler et al. | |
| 2010/0234888 | A1 * | 9/2010 | McClintock | A61B 17/1757 |
| | | | | 606/246 |
| 2012/0158059 | A1 | 6/2012 | Freid et al. | |
| 2012/0203284 | A1 * | 8/2012 | Khanna | A61B 17/8004 |
| | | | | 606/286 |
| 2012/0277749 | A1 * | 11/2012 | Mootien | A61B 17/8875 |
| | | | | 606/70 |
| 2014/0277490 | A1 * | 9/2014 | Perloff | A61F 2/4455 |
| | | | | 623/17.16 |
| 2014/0316472 | A1 * | 10/2014 | Rise | A61B 17/8085 |
| | | | | 606/280 |
| 2016/0143664 | A1 * | 5/2016 | Garcia | A61B 17/808 |
| | | | | 606/70 |
| 2017/0079685 | A1 * | 3/2017 | Dirisio | A61B 17/8023 |
| 2018/0271572 | A1 * | 9/2018 | Whyne | A61F 2/2875 |
| 2020/0289271 | A1 * | 9/2020 | Nedrud | A61F 2/2803 |

* cited by examiner

EXPANDABLE MEDICAL IMPLANT FOR ADOLESCENT CRANIUM DEFECTS

CROSS-REFERENCE TO RELATED APPLICATIONS

This claims priority to U.S. Patent Application Ser. No. 63/030,482 filed on May 27, 2020, the disclosure of which is hereby incorporated by reference as if set forth in its entirety herein.

FIELD OF THE INVENTION

Embodiments of the present invention relate generally to expandable medical implants, and more specifically, to medical implants for repair of cranium defects in adolescent patients.

BACKGROUND

Surgical procedures to correct cranial defects such as a tumor removal involve creating a void in the patient's cranium. For instance, a section of the patient's cranium may be removed to access and remove the tumor, thereby exposing a bone void in the cranium. In other examples, surgical procedures to address cranial trauma, such as cranial fractures, can involve fixation of cranial bone fragments to the cranium on opposite sides of the fracture or fractures. Cranial surgical procedures often include treating the cranium with implants that can reconstruct or substitute for the bones to restore and maintain normal function and appearance.

Conventional cranial implants such as the cranial implant 20 shown in FIG. 1 have successfully protected underlying critical structures, like the brain and dura mater, and have produced desirable clinical outcomes. The cranial implant 20 has a cranial implant body 22 that defines an inner bone-facing surface 24*a* and an outer surface 24*b* opposite the inner surface 24*a*. The cranial implant 20 further includes a plurality of bone fixation holes 23 that are configured to receive respective bone fixation elements that fix the cranial implant 20 to an underlying skull 29 of a patient's cranium 26, such that the implant 20 generally conforms to the outer surface 27 of the cranium 26. The cranial implant 20 can thus span a cranial defect that can be configured as a bone void or one or more bone fractures.

In some examples, cranial implants are commercially available as generic implants that are bent and/or cut to be sized for the patient to be treated. In other examples, patient-specific cranial implants can be custom produced for the patient to be treated. For instance, the cranial implants can be designed to fit a virtual model of the cranium based on one or more scans of the cranium, and subsequently manufactured. As a result, the patient-specific cranial implant requires little or no manipulation or cutting prior to implantation compared to generic implants. The present inventors have discovered that a need remains for a cranial implant that allows for patient skull growth after implantation of the cranial implant.

SUMMARY

In one example, an expandable bone implant can include a plurality of interconnected links including at least one hub and a plurality of peripheral links. At least two of the interconnected links can define respective bone fixation holes that are configured to receive respective bone fixation elements so as to fix the at least two of the links to an underlying bone. The implant can further include a plurality of connectors connected to the hub and respective different ones of the plurality of peripheral links, such that the peripheral links are spaced from the hub in different directions. The connectors permit expansion of the implant from a first size to a second size in response to growth of the underlying bone, wherein the hub and at least some of the plurality of peripheral links are spaced apart from each other respective first distances at the first size, and the hub and the at least some of the at least some of the plurality of peripheral links are spaced apart from each other a second distance at the second size, the second distance being greater than the first distance.

BRIEF DESCRIPTION OF THE DRAWINGS

The drawings illustrate generally, by way of example, but not by way of limitation, various embodiments discussed in the present disclosure. The foregoing summary, as well as the following detailed description of preferred embodiments of the application, will be better understood when read in conjunction with the appended drawings.

DETAILED DESCRIPTION

Figure 1:
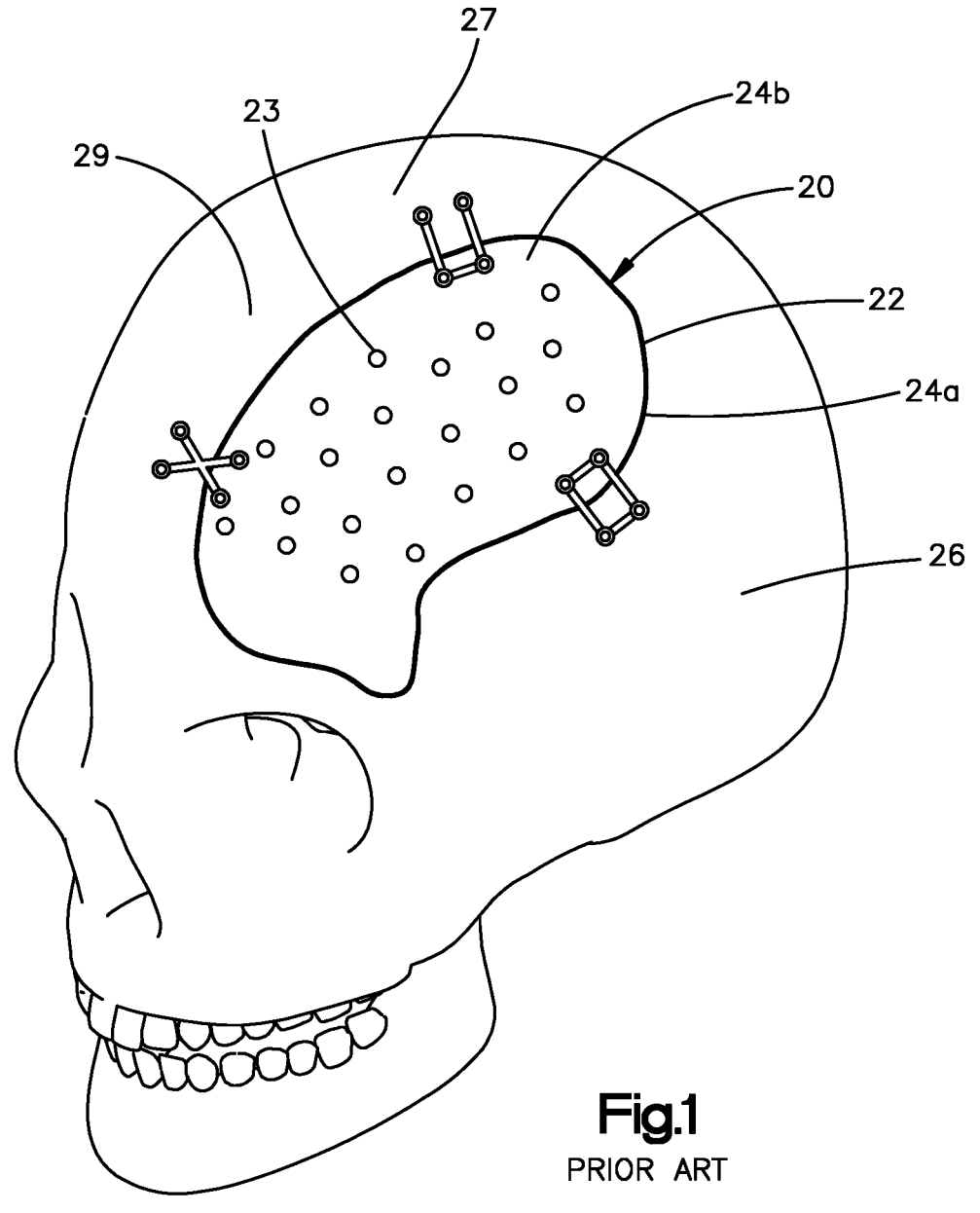
FIG. 1 is a perspective view of a cranial implant fixed to an underlying cranium in accordance with the prior art.

As used herein, singular terms as applied herein to apparatus and method steps can apply with equal force and effect to a plurality or at least one of the apparatus and method step, unless otherwise indicated. Similarly, a plurality as applied to herein to apparatus and methods can apply to the singular apparatus and method step, or at least one of the apparatus and method step, unless otherwise indicated. The terms "substantially," "approximately," derivatives thereof, and words of similar import as used herein with respect to a value, size, shape, direction, location, or other parameter, can include the stated value, size, shape, direction, and location, or other parameter, and variances up to 10% of the stated value, size, shape, direction, and location, or other parameter, including 8%, 5%, 3%, 2%, and 1%, unless otherwise indicated.

Referring to FIGS. 2A-2D generally, the present disclosure describes examples of expandable anatomical implants 30 that can be implanted onto one or more anatomical structures to stabilize the one or more anatomical structures to promote healing. For instance, the implants 30 can be implanted onto one or more bones 25 to stabilize one or more bone defects of the one or more bones 25. In one example, the bone 25 is a cranium 26 of an adolescent patient, and in particular can be a skull 29 of the cranium 26.

Figures 2A, 2B:
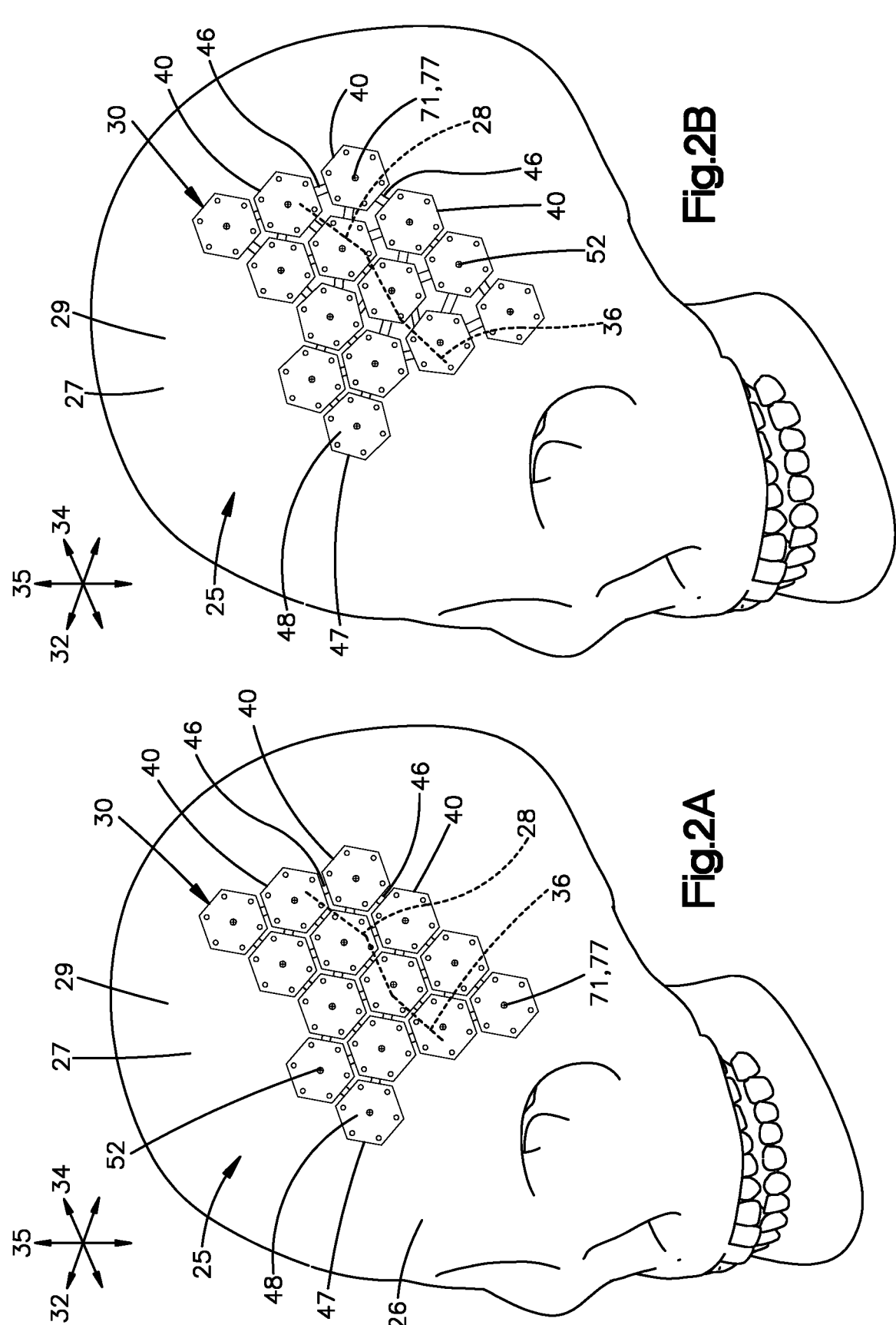
FIG. 2A is a perspective view of an expandable cranial implant of one example fixed to an underlying cranium and extending across a first cranial defect, and shown in an unexpanded state.
FIG. 2B is a perspective view of the expandable cranial implant of FIG. 2A shown in an expanded state.
Figures 2C, 2D:
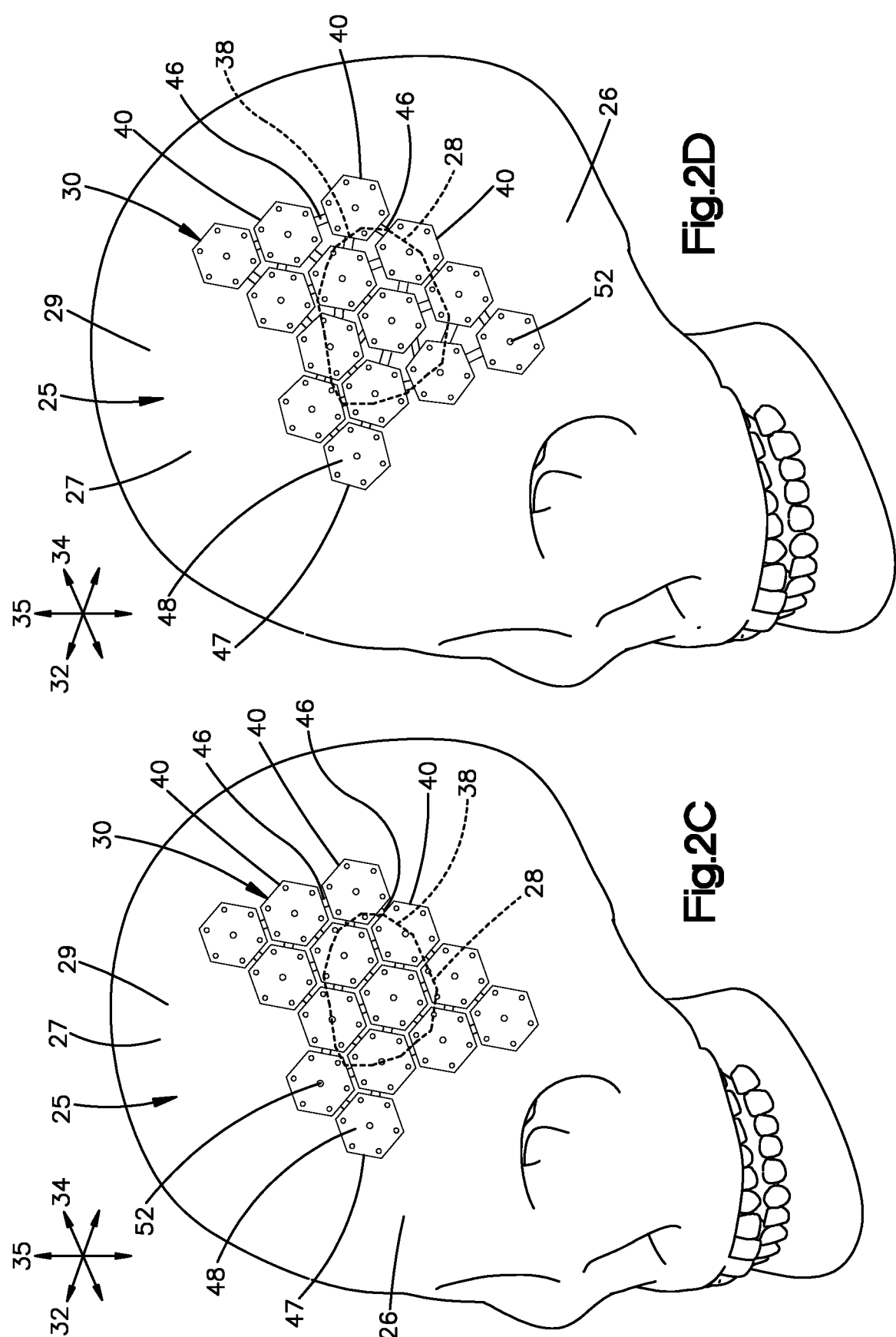
FIG. 2C is a perspective view of an expandable cranial implant of one example fixed to an underlying cranium and extending across a second cranial defect, and shown in an unexpanded state.
FIG. 2D is a perspective view of the expandable cranial implant of FIG. 2C shown in an expanded state.

The implants 20 can be designed and configured to be implanted onto bones 22 that will grow over time. In this regard, the present inventors have recognized that when a surgical procedure is performed on a still developing cranium, such as that of an adolescent patient, the cranium 26 can grow over time long after the surgical procedure has been performed. Accordingly, the implants 20 can advantageously be expandable so as to expand with the underlying bone or bones 22 as they grow over the years. In one example, the anatomical implants 20 described herein can be configured as expandable implants 30 that are configured to be implanted onto the cranium 26 of an adolescent patient. The implant 30 is expandable in at least one direction of expansion, such as a plurality of different directions of expansion, from a first or unexpanded state (FIGS. 2A and 2C) having a first size to a second or expanded state (FIGS. 2B and 2D) having second size greater than the first size to allow for continued growth of the cranium 26 during brain development, as well as to allow for to satisfactory anatomical fixation and associated healing. The cranium 26 illustrated in FIGS. 2A and 2C is shown with a bone defect 28. The implant 30 has been fixed to the cranium 26 at opposed sides of the bone defect 28 to stabilizing the defect 28 and promote healing.

The cranium 26, and in particular the skull 29, defines a curved or generally convex outer surface 27 that extends along a first or medial-lateral direction 32, a second or anterior-posterior direction 34 that is oriented perpendicular to the first direction, and a third or the superior-inferior direction 35 that is oriented perpendicular to each of the medial-lateral direction 32 and the anterior-posterior direction 34. The implant 30 is fixed to the cranium 26 such that it extends along the outer surface 27. Over time, the cranium 26, including the outer surface 27, of an adolescent human can expand in one or more up to all of the directions 32, 34, and 35. The cranial implant 30 affixed to the cranium can advantageously be expandable along with the cranium 26 in all of the directions of expansion without compromising fixation of the cranial implant 30 to the cranium 26.

The cranial implant 30 can include a plurality of orthopaedic links 40 that are moveably coupled to each other by respective connectors 46, such that the links 40 can be movable with respect to each other as the underlying cranium 26 expands over time. Expansion of the implant 30 can be continuous and stepless in certain examples, such that the implant 30 can expand from a first unexpanded state to a second expanded state. The second expanded state can be determined to be greater than the expected expansion of the cranium 26 over time, in order to ensure that the implant 30 remains expandable as the cranium 26 expands to its fully expanded size. The implant 30, and the components of the implant 30, can be made from any suitable biocompatible material as desired, such as a biocompatible metal, a biocompatible resorbable or non-resorbable polymer, or a combination thereof, including but not limited to titanium, stainless steel, alloys thereof, polyetheretherketone (PEEK), polyetherketoneketone (PEKK), or any suitable alternative biocompatible material as desired. In still other examples, the implant 30, and components of the implant 30, can be made using any suitable combination of organic and non-organic materials. For instance, the implant 30 and components of the implant 30 can be made from an organic demineralized bone matrix with organic stem cells. In other examples, the implant 30 and components of the implant 30 can be made from an organic demineralized bone matrix with a non-organic internal polymer structure. In still other examples, the links 40 can be made from a non-organic metal, and the connectors 46 can be made from a suitable polymer.

In one example, the links 40 can be flexible so as to substantially conform to the outer surface 27 of the cranium 26. Alternatively, the links 40 can be manufactured having a curvature so as to generally conform to the outer surface 27 of the cranium 26. The links 40 can then be flexed or bent as desired to improve the fit to the outer surface 27 of the cranium. In still other examples, the links 40 can be manufactured to be patient-specific, and thereby to manufactured to conform to the outer surface 27 of the cranium 26 based on images that have been taken of the cranium 26. In particular, the links 40 can be designed to conform to virtual images of the cranium 26, and subsequently manufactured.

As illustrated in FIG. 2A, the defect 28 of the cranium 26 is shown as a fracture 36 that can be the result of a trauma or other condition. The implant 30 can be implanted onto the cranium, such that the implant 30 is fixed to the cranium 26 on opposite sides of the fracture 36. Thus, the implant 30 extends across the defect 28. As shown at FIG. 2B, the bone fracture 36 has healed and the cranium 26 has expanded over time. Referring to FIG. 2C, in another example the defect 28 can be configured as a bone void 38 that can be the result of a trauma, surgery, or other condition. The implant 30 of FIG. 2C can be implanted onto the cranium 26, such that the implant 30 extends over and covers the bone void 38, and is fixed to the cranium 26. Thus, the implant 30 extends across the defect 28. As shown at FIG. 2D, the bone void 38 has healed and the cranium 26 has expanded over time. In both FIGS. 2A and 2C, the implant 30 can be implanted having the first size as described above. As shown in FIGS. 2B and 2D, the interconnected links 40 remain interconnected, but have moved away from each other along both the longitudinal direction L and the lateral direction A in order to accommodate expansion of the underlying bone. Thus, the implant 30 has expanded along with the cranium 26 from the first size to the second size that is greater than the first size.

As will be appreciated from the description below, the implants 30 described herein can be suitable for the pediatric population, stable in maintaining the shape of the cranium, protective of the brain by covering the bone defect, and are configured to be fixed to the cranium 26. Further, the cranial implants 30 described herein can be configured to expand in all of the directions in which the underlying cranium 26 of expands as the cranium 26 develops and grows, while at the same time providing protection to the underlying anatomical structures such, as the brain and dura mater. In particular, the implant 30 can expand in one direction, multiple directions, radially, spherically, and/or in a data determined orientation. The implant 30 can be particularly suitable for fixation to the cranium 26 of an adolescent patient to accommodate expansion of the cranium 26 until the cranium 26 is fully grown.

Examples of such implants 30 will now be described in detail, with reference to FIGS. 2A-3D. In particular, the implant can include a plurality of interconnected links 40 that are movable with respect to each other so as to permit expansion of the implant from the unexpanded state to the expanded state as the underlying bones 22 expands. As described above, the bone 22 can be configured as a cranium 26. Thus, the implant 30 can be referred to in some examples as a cranial implant that is configured to be implanted onto either or both of the cranial and craniofacial bones of the cranium 26. In one example, the cranial implant is configured to be attached to a skull 29 of a patient. Each of the links 40 can define a bone-facing surface 47 and an outer surface 48 that is opposite the bone-facing surface 47 along a transverse direction. The bone-facing surfaces 47 can further abut the underlying outer surface 27 of the cranium 26. The bone-facing surfaces 47 of the links 40 can combine to define a bone-facing surface of the implant 30 that faces the outer surface 27 of the cranium 26, and the outer surfaces 48 of the links 40 can combine to define an outer surface of the implant 30.

Each of the links 40 defines an outer perimeter 50 that extends between the respective bone-facing surface 47 and the respective outer surface 48. The outer perimeter 50 can define a shape with respect to either or both of a plan view of the bone-facing surface 47 along the transverse direction, and a plan view of the outer surface 48 along the transverse direction. The outer perimeters 50 of the plurality of interconnected links 40 can be substantially identical to each other so as to achieve a substantially uniform expansion profile. It is appreciated, of course, that the outer perimeters 50 of the interconnected links 40 can alternatively differ from each other as desired.

The outer perimeters 50 of the links 40 can be configured as plates that have any suitable shape as desired. In one example, the outer perimeters 50 can have at least one straight side. For instance, the outer perimeters can substantially define a polygon having any number of sides 51 as desired. The polygon can be a regular polygon in some examples whereby the sides 51 have substantially equal lengths. For instance, while the outer perimeters 50 are illustrated as hexagons having six sides 51 in FIGS. 2A-3D, the polygon can alternatively be configured as a triangle having three sides 51, a square having four sides 51, pentagon having five sides 51, heptagon having seven sides 51, an octagon having eight sides 51, a nonagon having nine sides 51, decagon having ten sides 51, a hendecagon having eleven sides 51, a dodecagon having twelve sides 51, or any suitable alternative regular polygon having any number of sides 51 as desired. In other examples, the polygon can be an irregular polygon. In still other examples, the outer perimeters 50 can be round, such as oval-shaped, racetrack-shaped, or circular as desired. In still other examples, the outer perimeters can have an organic or original shape, such as an anatomical shape. In still other examples, the outer perimeter can be amorphous, such that at least one side of the outer perimeter is anatomically shaped. At least one up to all of the sides 51 of the links 40 can be configured to be movably connected to another one of the links 40 so as to produce the cranial implant 30 can having a plurality of interconnected links 40. In certain embodiments, the outer sides of the links may be contoured or trimmed to match a desired anatomical fit. Further, in some examples, the interconnected links 40 can nest with each other when the cranial implant 30 is in its unexpanded state. Thus, the interconnected links 40 can have the same shape in some examples. It should be appreciated, however, that the at least some of the interconnected links 40 can have different shapes than each other. Each of the interconnected links 40 can have any suitable size as desired. In one example, the links 40 can define a maximum cross-sectional dimension in a plane that can be in a range from approximately 0.5 cm to approximately 2.5 cm, such as from approximately 1 cm to approximately 1.5 cm.

With continuing reference to FIGS. 2A-3D, the links 40 can be movably coupled to each other such that the implant 30 is expandable the unexpanded state to the expanded state. In particular, the implant 30 can include a plurality of connectors 46 that are connected to respective first and second interconnected links 43 and 45 that define respective pairs 41 of the interconnected links 40. In particular, the connectors 46 each extend along a respective first direction of extension that can be defined as a direction from the second link 45 to the first link 43 along the direction of expansion, and a second direction of extension that can be defined as a direction from the first link 43 to the second link 45 along the direction of expansion. The connectors 46 are configured to permit movement of respective first and second interconnected links 43 and 45 of each pair 41. The first and second links 43 and 45 can be configured as immediately adjacent links, meaning that there are no intervening links between the immediately adjacent first and second links 43 and 45. In one example, the connectors 46 extend out from respective sides of the links 40 of each respective pair 41 of links 40. For instance, each of the connectors 46 can extend out from a respective side of an interconnected link 40 along a direction that is perpendicular to the respective side, or along any suitable alternative direction that is angularly offset with respect to the respective side. The implant 30 can include connectors 46 that extend out from each side of the interconnected links 40. Alternatively, the connectors 46 can extend out from some but not all of the sides of the interconnected links 40. The connectors 46 can be substantially identically shaped as desired.

In one example, the connectors 46 can be flexible so as to substantially conform to the outer surface 27 of the cranium 26. Alternatively, the connectors 46 can be rigid and manufactured having a suitable shape to correspond to the underlying cranium, and further having a suitable shape to translate in one or both of the channels of the first and second links 43 and 45, respectively, as described herein.

The links 40 of each pair 41 of interconnected links 40 can be spaced from each other in respective directions of expansion a first distance D1 when the implant 30 is in the unexpanded state, and can move away from each other along the respective directions of expansion such that the links 40 are spaced apart from each other in the respective directions a second distance D2 when the implant 30 is in the fully expanded state. The second distance D2 is thus greater than the first distance D1 by an individual expansion distance that can be in a range from approximately 0.5 mm to approximately 2 mm. The individual expansion distance can be determined based on the desired total expandability of the implant 30, and the number of interconnected links 40 included in the implant 30. It is recognized that in some examples, the links 40 can abut each other when the implant 30 is in the unexpanded state, and thus the first distance D1 can be zero. The implant 30 can be said to be in an expanded state when the links 40 of at least one of the pairs 41 of interconnected links 40 are spaced from each other a distance greater than the first distance D1. The individual expansion distances can be substantially equal to each other or different from each other as desired. Thus, the expandability of the implant 30 in one direction can be equal to or different than the expandability of the implant 30 in a different direction.

Some of the respective directions can be a common direction. That is, the links 40 of some of the pairs 41 of interconnected links 40 can be spaced from each other along the common direction, and can therefore move away from each other in the common direction along respective individual expansion distances. Thus, the implant 30 is expanded along the common direction a total expansion distance that is a sum of each of the individual expansion distances in the common direction. In other examples, the links 40 of at least some of the pairs 41 of interconnected links 40 can be spaced from each other in different directions. The pairs 41 of interconnected links 40 that are spaced from each other in the different directions can therefore move apart in the different directions, thereby expanding the implant 30 in the different directions. When the implant 30 assumes a curved shape, such as that when the implant is attached to a skull (i.e., the bone-facing surface 47 is concave), expansion of the implant can also include a directional component that is oriented along the transverse direction that extends from the outer surface 48 toward the bone-facing surface 47. When a direction of expansion of a pair 41 of links is along a unique direction that is not in common with the direction of expansion of any other pairs 41 of links, the total expansion distance of the implant 30 in the unique direction is equal to the individual expansion distance in the unique direction of expansion.

The links 40 can define a plurality of different directions of expansion, depending on the shape of the links 40. For instance, in an example whereby the links 40 define polygons having an even number of sides, the implant 30 can define a number of directions of expansion that are one half the number of sides. For instance, when the links 40 define hexagons as shown in FIGS. 3A-3D having three pairs of sides that are opposite and parallel to each other in respective directions, the implant 30 can define three directions. While the implant 30 is shown in a planar orientation in FIG. 3A for illustrative purposes, it is recognized that the implant 30 can be curved to fit the underlying cranium during use. Further, the hexagonal link (and regular polygon having an even number of sides) provide for bidirectional expansion in each of the directions. In an alternative example, whereby the polygons have an odd number of sides, the implant 30 can define a number of directions of expansion that is equal to the number of sides. For instance, when the links 40 define triangles whereby no sides are opposite and parallel to each other in any directions, the implant 30 can define similarly define three directions of expansion. However, the triangle (or other polygon having no opposed sides that are oriented parallel to each other) defines unidirectional expansion along the directions of expansion. It should be appreciated that the implant 30 can be configured to expand along any number of directions of expansion as desired. Otherwise stated, the respective common directions can be defined by the direction of extension of the connectors 46 from the first link 43 of the respective pair 41 to the second link 45 of the respective pair. Thus, the links 40 can define up to four directions of expansion, up to five directions of expansion, up to six directions of expansion, and so forth.

Because the implant 30 includes a plurality of interconnected links 40, the implant can expand a total expansion distance in the respective different common directions that each is the sum of the individual expansion distances of the plurality of links 40 in each of the respective common directions. The implant 30 can include any number of interconnected links 40 as desired, depending for instance on the size and nature of the cranial defect. For instance, the larger the cranial defect, the more interconnected links 40 included in the medical implant. Greater numbers of interconnected links 40 can also provide for a greater total expansion distance.

In one example, the interconnected links 40 can be arranged as at least one hub 42 and a plurality of peripheral links 44 that are movably coupled to each other. In particular, respective connectors 46 can be movably connected to at least one of the hub 42 and a respective different one of the peripheral links 44. Thus, the hub 42 can be movably coupled to the respective different ones of the peripheral links 44. Thus, the hub 42 can define the first link 43 of the pair 41 of interconnected links 40, and one of the peripheral links 40 can define the second link 45 of the pair 41 of interconnected links 40. Alternatively, the hub 42 can define the second link 45 of the pair 41 of interconnected links 40, and one of the peripheral links 40 can define the first link 43 of the pair 41 of interconnected links 40. A hub 42 can be referred to as one of the interconnected links 40 that is movably connected to a plurality of peripheral links 44 in different directions. Peripheral links 44 can thus be referred to as a plurality of the interconnected links 40 that are connected to a common hub 42 in different directions. In this regard, it should be appreciated that some of the interconnected links 40 can define both a hub 42 and a peripheral link 44. For instance, a plurality of the links 40 can be coupled to a plurality of other links 40. In one example, implant 30 thus includes a plurality of hubs 42 that are all interconnected to at least one, such as a plurality (e.g., two or more) peripheral links 44. In particular, the interconnected links 40 can define respective central axes 52 that extend along the transverse direction the bone-facing surfaces 47 to the outer surfaces 48, and the central axis 52 of the hub 42 is spaced from the central axes 52 of the peripheral links 44 in the different respective expansion directions that are angularly offset from each other. For instance, the different respective directions can be non-parallel to each other and non-perpendicular to each other. The different respective directions can define the respective expansion directions along which the peripheral links 44 and the hub 42 move away from each other. Because the peripheral links 44 are movably connected to a common hub 42 in multiple directions, the implant 30 can be expanded in a total expansion distance in each of the multiple directions in the manner described above. In one example, the hub 42 and peripheral links 44 can define a plurality of pairs 41 of interconnected links 40. The hub 42 can define the first link 43 of each of the respective pairs, and the peripheral links 44 can define the second links 45 of the respective pairs.

Figures 3A, 3B:
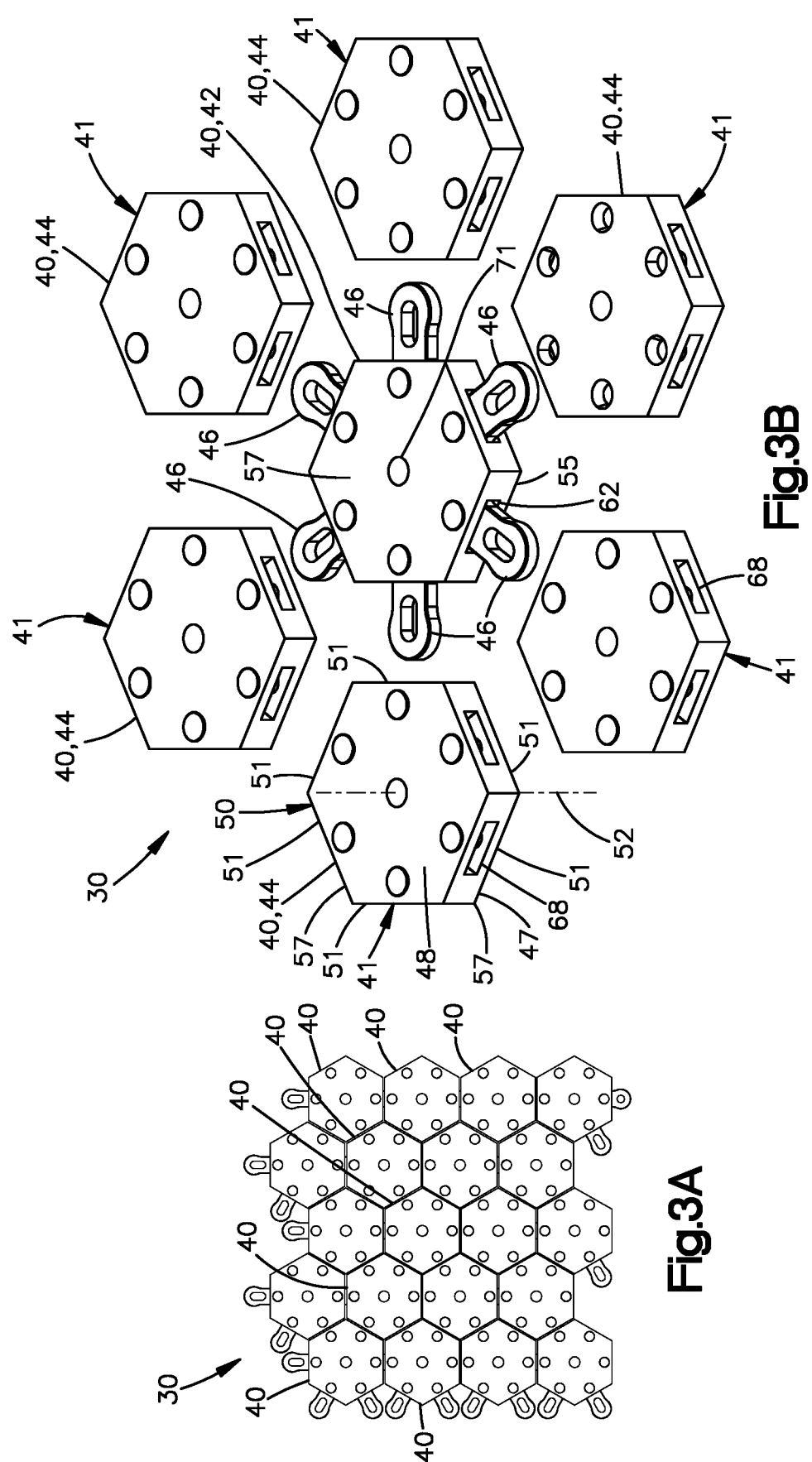
FIG. 3A is a top plan view of an expandable cranial implant including a plurality of interconnected links and a plurality of connectors that are connected between the interconnected links.
FIG. 3B is a perspective view of a hub and a plurality of peripheral links of the implant shown in FIG. 3A.
Figure 3C:
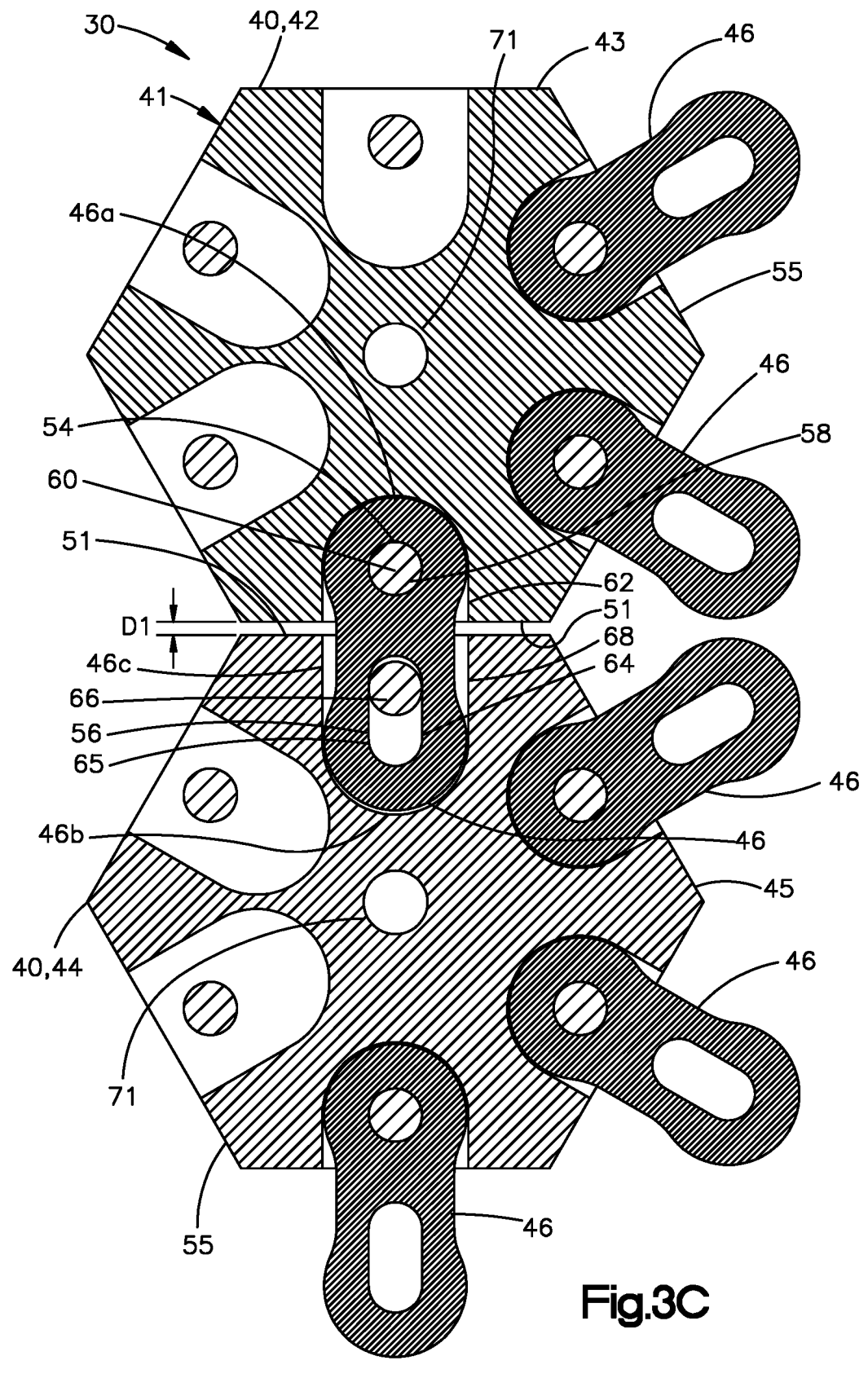
FIG. 3C is a perspective view of the hub and a peripheral link of the plurality of peripheral links of FIG. 3A, shown prior to expansion.
Figure 3D:
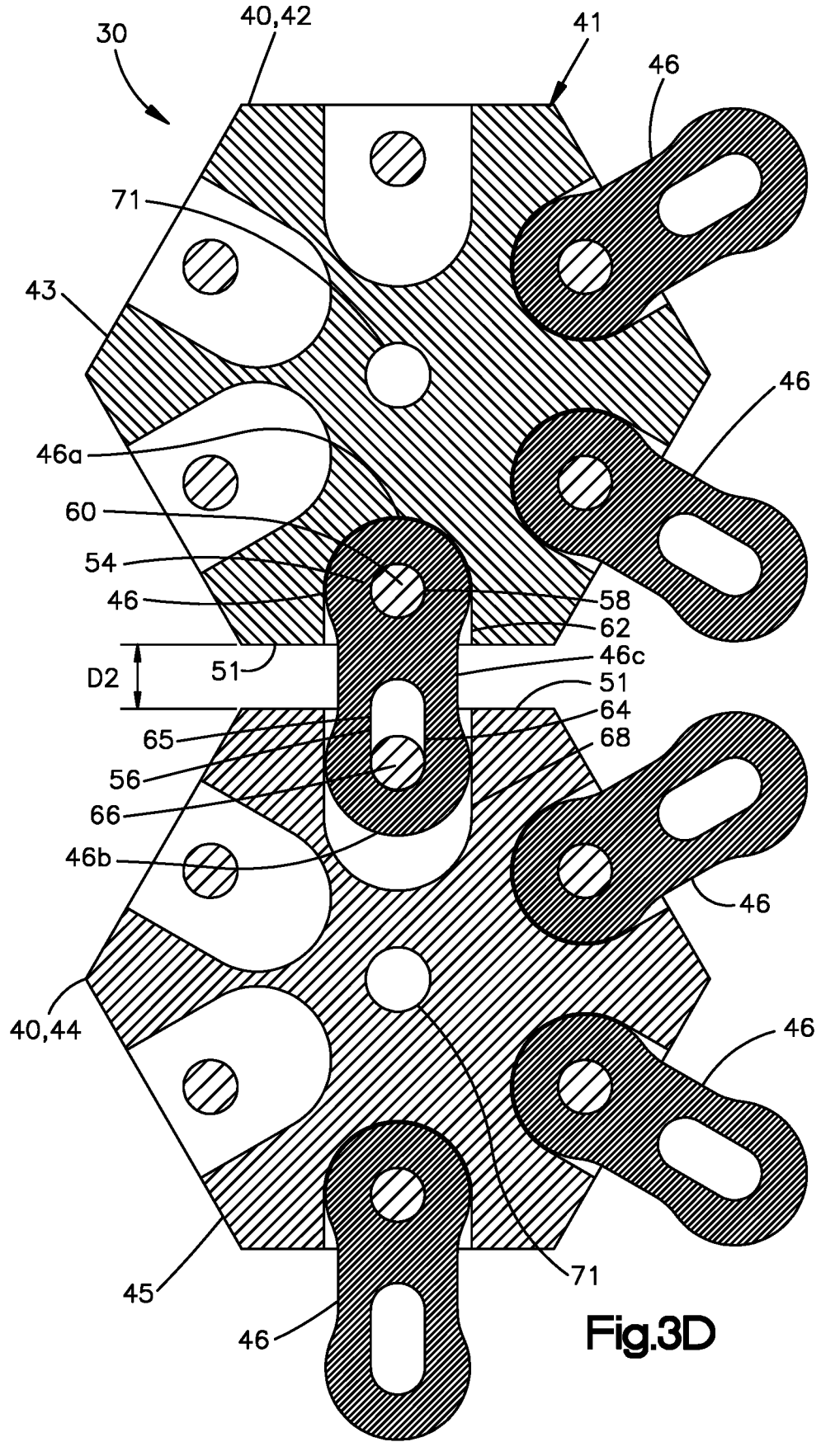
FIG. 3D is a perspective view of the hub and the peripheral link of FIG. 3C, shown after expansion.

In particular, referring now to FIGS. 3C-3D, the connectors 46 can be translatably attached to at least one or both of the first 43 and second 45 interconnected links 40 of the pair 41 so as to translatably couple the first link 43 to the second link 45, thereby allowing at least one of the links 40 to move away from the other of the links 40 along the respective directions of expansion, which thereby expands the implant 30 in response to expansion of the underlying cranium 26 when the implant 30 is fixed to the underlying cranium 26. When the implant 30 is in the unexpanded state, the hubs 42 and the respective peripheral links 44 are spaced apart from each other by the first distance D1. When the implant 30 is expanded from the unexpanded state, at least one of the hubs 42 and the respective at least one of the peripheral links 44 is spaced from each other by a distance greater than the first distance D1. When the implant 30 is in the fully expanded state with respect to a direction, all hubs 42 and all respective peripheral links 44 are spaced apart from each other by the second distance D2 in the respective direction. When the implant 30 is in the fully expanded state with respect to all directions, all of the hubs 42 and all of the respective peripheral links 44 are spaced from each other by the second distance D2 in all directions.

The connectors 46 can each define a respective first connection member 54 that is configured to be connected to a complementary first connection member of the first interconnected link 43 of the respective pair 41, and a second connection member 56 opposite the first connection member 54 and configured to be connected to a complementary second connection member of the second interconnected link 45 of the respective pair 41. The first and second connection members 54 and 56 can be opposite each other along the expansion direction. The connector 46 can thus be elongate along the direction of expansion. At least one of the first and second members 54 and 56 can be movably connected to the respective first and second links 43 and 45. In one example, the first connection member 54 can define a first aperture 58 that extends therethrough along the transverse direction, and the complementary first connection member of the first link 43 is configured as a first retention pin 60. Thus, the first aperture 58 can be configured to receive the first retention pin 60 of the first link 43.

Figure 4A:
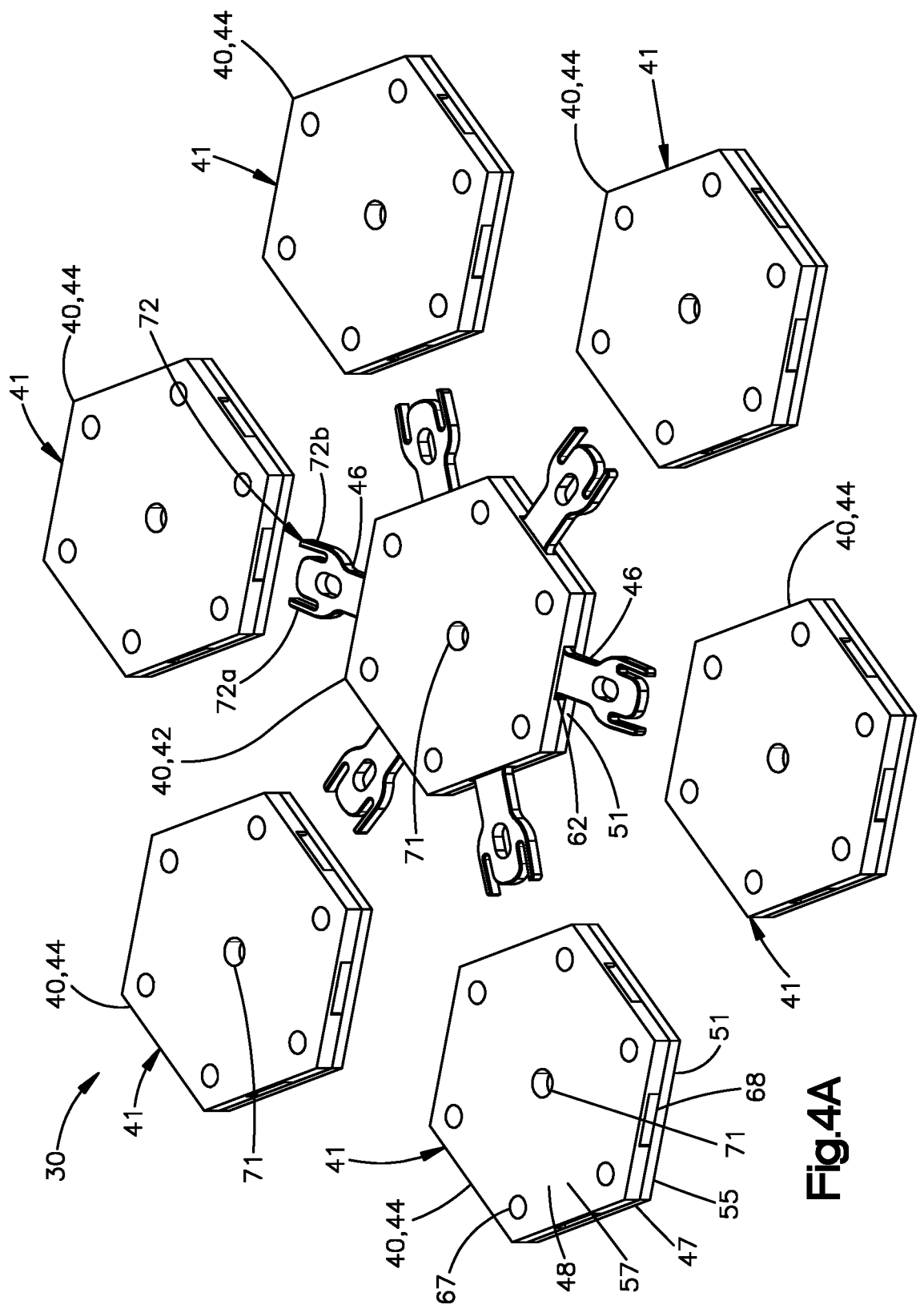
FIG. 4A is a perspective view of an expandable implant in another example, including a hub and a plurality of peripheral links.
Figure 4B:
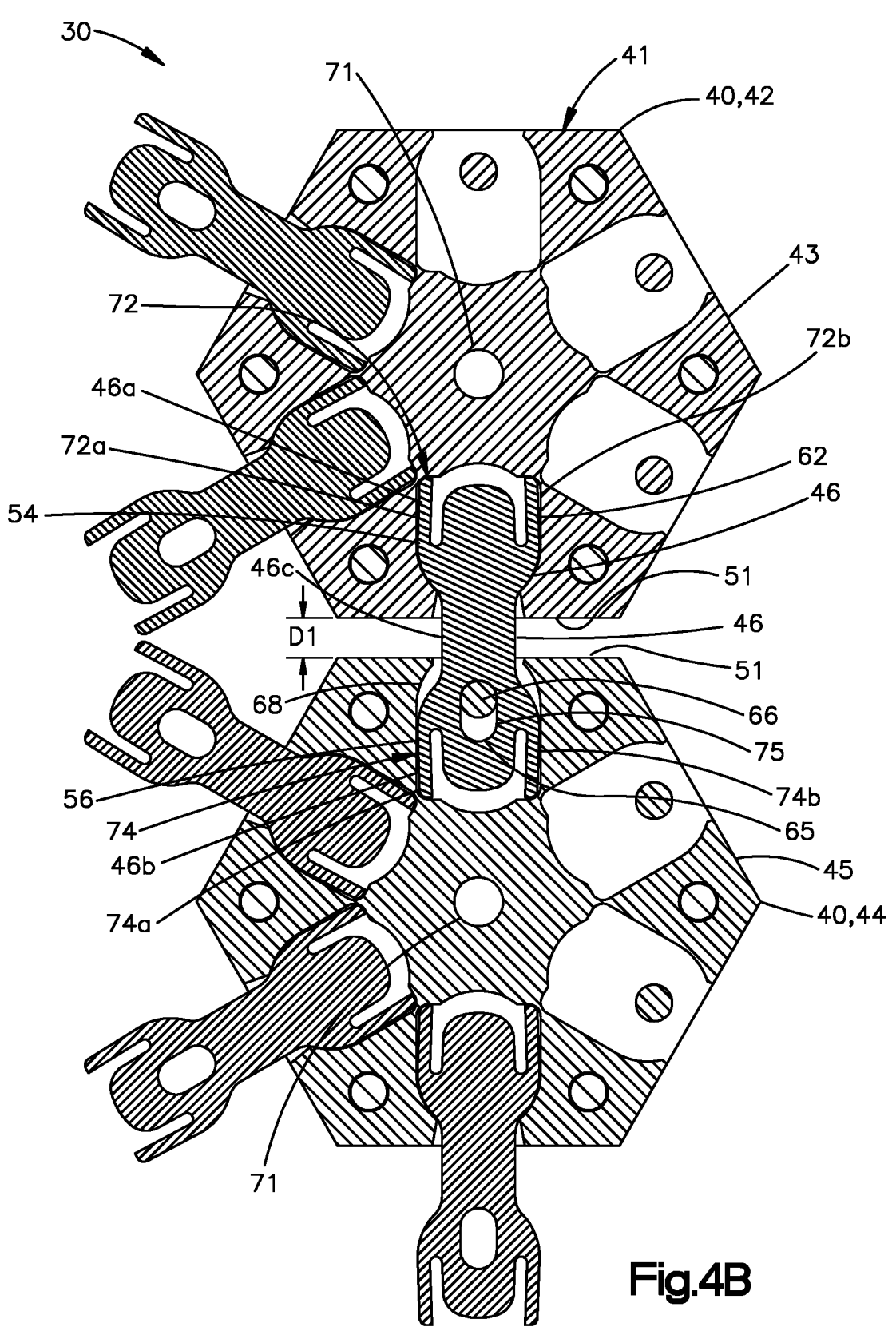
FIG. 4B is a perspective view of the hub and a peripheral link of the plurality of peripheral links of FIG. 4A, shown prior to expansion.
Figure 4C:
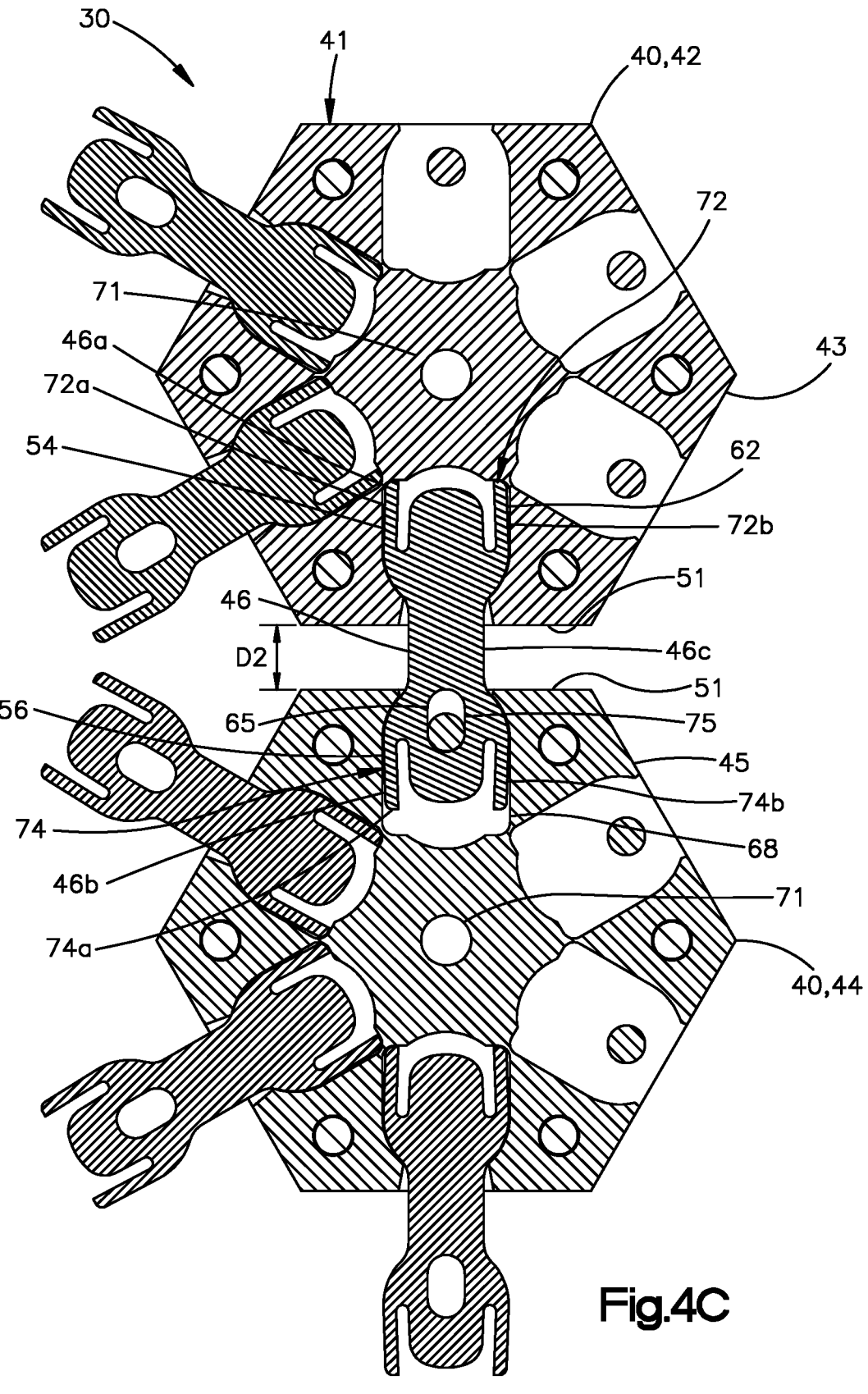
FIG. 4C is a perspective view of the hub and the peripheral link of FIG. 4B, shown after expansion.

In particular, the first link 43 can define a first channel 62 that extends into a respective side 51 of the first link 43 toward the central axis 52. A first end 46a of the connector 46 that defines the first aperture 58 can be received in the first channel 62. The first retention pin 60 can extend along the transverse direction through the first channel 62 and also through the first aperture 58, thereby attaching the connector 46 to the first link 43. The first aperture 58 can be sized in cross-section substantially equal to the first retention pin 60, such that the first retention pin 60 (and thus the first link 43) is substantially fixed with respect to translation relative to the connector 46. The first link 43 can define a base 55 that defines the bone-facing surface 47, and a cover 57 that defines the outer surface 48, such that the first channel 62 is disposed between the base 55 and the cover 57 along the transverse direction. The base 55 and cover 57 can define a single monolithic structure as illustrated in FIG. 3B, or can be separate and attached to each other by any suitable fastener 67 as illustrated in FIG. 4A.

The retention pin 60 can be rotatable in the first aperture 58 so as to define a first pivot axis that is oriented along the transverse direction. The connector 46 and the first link 43 can thus be pivotable with respect to each other about the first pivot axis. Alternatively, the connector 46 and the first channel 62 can be shaped (and/or the first aperture 58 and the first retention pin 60 can be shaped) such that the connector 46 and the first link 43 are not pivotable with respect to each other. It should be appreciated that the first link 43 can include a plurality of respective first channels 62 that extend into one or more up to all of the sides 51, and respective first retention pins 60. Thus, a plurality of connectors 46 can be received in the plurality of first channels 62, respectively, so as to connect the connectors 46 to the first link 43. While the first connection member 54 is translatably fixed to the first link 43 in one example, the first connection member 54 can alternatively be movable, and in particular translatable, with respect to the first link 43 in another example, as will now be described with respect to the second connection member 56.

In particular, the second connection member 56 can define a second aperture 64 that extends therethrough along the transverse direction, and the complementary second connection member of the second link 45 can be configured as a second retention pin 66. Thus, the second aperture 64 can be configured to receive the second retention pin 66 of the second link 45. In particular, the second link 45 can define a second channel 68 that extends into a respective side 51 of the second link 45 toward the central axis 52. A second end 46b of the connector 46 that defines the second aperture 68, and is opposite the first end 46a, can be received in the second channel 68. The connector 46 further defines a body 46c that extends between the first and second ends 46a and 46b. The second retention pin 66 can extend along the transverse direction through the second channel 68 and also through the second aperture 68, thereby attaching the connector 46 to the second link 45. The second link 45 can define a base 55 that defines the bone-facing surface 47, and a cover 57 (see FIG. 3A) that defines the outer surface 48, such that the channel 68 is disposed between the base 55 and the cover 57 of the second link 45 along the transverse direction. The base 55 and cover 57 of the second link 45 can be separate and attached to each other, or can define a single monolithic structure as desired.

The second aperture 64 can be elongate along the direction of expansion, and longer than the second retention pin 66 along the direction of expansion. In this regard, the second aperture 64 can be referred to as an elongate slot 65.

The elongate slot 65 can be fully enclosed as desired. Thus, the second retention pin 66 can move, and in particular can translate, in the second aperture 64 along the respective direction of expansion. As a result, the second connection member 56, and thus the connector 46, can move in the first direction of extension toward the first link 43, which causes the first and second links 43 and 45 to move away from each other along the respective direction of expansion as the underlying cranium 46 grows and expands. When the second retention pin 66 is disposed at a first end 64a of the second aperture 64, the first and second links 43 and 45 define the first distance D1. When the second retention pin 66 is disposed at a second end 64b of the second aperture 64 opposite the first end 64a, the first and second links 43 and 45 are spaced apart from each other in the respective expansion direction the second distance D2. Thus, the connector 46 can be movable, for instance translatable, in the second channel 68 as the implant 30 expands from the first size to the second size. The second aperture 64 can be sized to prevent movement of the retention pin 66 in the second aperture 64 in a direction angularly offset with respect to the respective expansion direction. Alternatively, the second aperture 64 can be sized to prevent movement of the retention pin 66 in both the expansion direction and a direction angularly offset, such as perpendicular, with respect to the respective expansion direction.

Therefore, one of the first and second connection members 54 and 56 defines the slot 65 that slidably receives the retention pin of one of the hub and the peripheral link, and the other of the first and second connection members 54 and 56 is translationally fixed to the other of the hub and the peripheral link. In particular, the other of the first and second connection members 54 and 56 defines the aperture 58 that receives the retention pin of the other of the hub and the peripheral link, thereby translationally fixing the connector 46 to the other of the hub and the respective peripheral link. Alternatively still, each of the first and second connection members 54 and 56 can define a respective slot 65, such that the connector 46 is translatable with respect to each of the first and second links 43 and 45. As described above, the implant 30 can include a plurality of peripheral links interconnected with the hub by respective connector members 26 in the manner described herein.

Further, the second retention pin 66 can be rotatable in the second aperture 64 so as to define a second pivot axis that is oriented along the transverse direction. The connector 46 and the second link 45 can thus be pivotable with respect to each other about the second pivot axis. Alternatively, the connector 46 and the second channel 68 can be shaped (and/or the second aperture 64 and the second retention pin 66 can be shaped) such that the connector 46 and the second link 45 are not pivotable with respect to each other. It should be appreciated that the second link 45 can include a plurality of respective second channels 68 that extend into one or more up to all of the sides 51, and respective second retention pins 66. Thus, a plurality of connectors 46 can be received in the plurality of second channels 66, respectively, so as to connect the connectors 46 to the second link 45. While the second connection member 56 is translatably coupled to the second link 45 in one example, the second connection member 56 can alternatively be translatably fixed to the second link 45 as described above with respect to the first link 43. It should further be appreciated that the first and second connection members 54 and 56, and the complementary connection members of the first and second links 43 and 45, can be structurally configured in accordance with any suitable alternative embodiment as desired. For instance, the complementary connection members can define apertures, and the first and second connection members 54 and 56 can define pins that are received in the apertures.

Any one or more of the interconnected links 40 can include a hole 71 that extends along the transverse direction from the outer surface 48 to the bone-facing surface 47. The hole 71 can be configured as a bone fixation hole 77 that is configured to receive a bone fixation member so as to secure the links 40 to the underlying cranium 26. In some examples, the bone fixation hole 77 can be unthreaded so as to receive a compression screw that fixes the links 40 to the underlying cranium 26. In other examples, the bone fixation hole 77 can be threaded and thus configured to threadedly purchase with a threaded head of a locking screw that fixes the links 40 to the underlying cranium 26. In some examples, at least two of the links 40 defines a respective bone fixation hole 77 so as to fix to the cranium 26 on opposed sides of the cranial defect. In other examples, at least some of the holes 71 can be a drainage hole that is configured to permit drainage through the link 40, and thus through the implant 30. Alternatively still, the hole 71 can receive stitching, suturing, or other securement members that can fasten the dura and/or temporal muscle to the respective link 40, and thus to the implant 30. The hole 71 can be centrally disposed in the respective link 40, or can be offset from the geometric center of the link 40 as desired.

While the first and second channels 62 and 68 can extend into the respective sides 51 at a location between the bone-facing surface 47 and the outer surface 48 in one example, it should be appreciated that either or both of the first and second channels 62 and 68 can be alternatively positioned as desired. For instance, either or both of the first and second channels 62 and 68 can extend into the respective bone-facing surface 47. In another example, either or both of the first and second channels 62 and 68 can extend into the respective outer surface 48.

Referring now to FIGS. 2A-2D and 4A-4C, the connector 46 can be translatably attached to at least one or both of the first and second links 43 and 45, thereby permitting movement of the first and second links 43 and 45 away from each other, in accordance with another example. For instance, the first connection member 54 can include a first pair 72 of first and second resilient retention arms 72a and 72b that are spaced from the body 46c and can extend substantially in the first direction of extension. Thus, the first connection member 54 can be devoid of an aperture that receives a retention pin of the first link 43 in some examples. The body 46c be disposed between the first arm 72a and the second arm 72b of the first pair 72. The first and second arms 72a and 72b of the first pair 72 can be resiliently compressible toward the body 46c. The first channel 62 can be sized to receive the first and second arms 72a and 72b of the first pair 72. In one example, the first and second arms 72a and 72b of the first pair 72 can be press-fit in the first channel 62, or otherwise disposed in the first channel 62. Thus, the first and second arms 72a and 72b of the first pair 72 can bear against the first link 43 at opposed sides of the first channel 62 so as to capture the connector 46 therein. The first channel 62 can be sized and shaped such that the connector 46 and the first link 43 are substantially fixed with respect to translation relative to each other. Further, the first channel 62 can define a neck proximate the side 51 that prevents or resists removal of the arms 72a and 72b from the first channel 62. Further, the connector 46 and the first link 43 can be substantially fixed with respect to pivoting or rotation relative to each other. Alternatively, the first connection member 54 can be translatable in the first channel 62 as will now be described with respect to the second connection member 56.

In particular, the second connection member 56 can include a second pair 74 of first and second resilient retention arms 74a and 74b that are spaced from the body 46c and can extend substantially in the second direction of extension. The body 46c be disposed between the first arm 74a and the second arm 74b of the second pair 74. The first and second arms 74a and 74b of the second pair 74 can be substantial mirror images of the first and second arms 72a and 72b of the first pair 72. The first and second arms 74a and 74b can be resiliently compressible toward the body 46c. The second channel 68 can be sized to receive the first and second arms 74a and 74b of the second pair 74. The first and second arms 74a and 74b of the second pair 74 can bear against the second link 45 at opposed sides of the second channel 68 so as to capture the connector 46 therein. In one example, the second channel 68 can be longer than the first and second arms 74a and 74b of the second pair 74, such that the first and second arms 74a and 74b are translatable in the second channel 68 along the direction of expansion. Thus, the connector 46 can be movable, for instance translatable, in the second channel 68 as the implant 30 expands from the first size to the second size. The second channel 68 can be sized to prevent movement of the first and second arms 74a and 74b in second channel 68 in a direction that is angularly offset with respect to the expansion direction. Alternatively, the second channel 68 can be sized to permit movement of the first and second arms 74a and 74b in the second channel 68 in the expansion direction and in a direction angularly offset, such as perpendicular, with respect to the respective expansion direction.

When the second connection member 56 is disposed at a first end of the second channel, the first and second links 43 and 45 define the first distance D1. When the second connection member 56 is disposed at a second end of the second channel 68 opposite the first end, the first and second links 43 and 45 are spaced apart from each other in the respective expansion direction the second distance D2. In addition, the connector 46 can include an aperture 75 as described above with respect to the second aperture 64 of FIGS. 3A-3D, and the second link 45 can include a retention pin 77 as described above with respect to the second retention pin 66 of FIGS. 3A-3D. Thus, the retention pin 77 can translate in the aperture 75 as the first and second links 43 move apart from the first distance D1 to the second distance D2. The second connection member 56, and thus the connector 46, can consequently move, such as translate, in the second direction of extension in the second channel 68. Alternatively, the second connection member 56 can be translatably fixed in the second channel 68 as described above with respect to the first connection member 54.

Referring now to FIGS. 2A-2D and 5A-5C, the connector 46 can be translatably attached to at least one or both of the first and second links 43 and 45, thereby permitting movement of the first and second links 43 and 45 away from each other, in accordance with another example. For instance, as described above at least one or both of the first pair 72 of first and second retention arms 72a and 72b and the second pair 74 of first and second retention arms 74a and 74b can be resilient. Thus, at least one or both of the first pair 72 of first and second retention arms 72a and 72b and the second pair 74 of first and second retention arms 74a and 74b can be resiliently flex and compress toward the body 46c. As a result, expansion of the underlying cranium 26 while the implant 30 is fixed to the cranium 26 provides a force that biases the first link 43 away from the second link 45. The first and second retention arms 72a and 72b of the first pair 72 can be press-fit in the first channel 62 in the manner described above. Further, the first channel 62 can be sized along the expansion direction substantially equal to the first connection member 54. Similarly, the first and second retention arms 74a and 74b of the second pair 74 can be press-fit in the first channel 62 in the manner described above. Further, the second channel 68 can be sized along the expansion direction substantially equal to the second connection member 56. The first and second channels 62 and 28 can extend into the outer surface 48 of the links 40 along the transverse direction, but can terminate along the transverse direction without extending through the bone-facing surface 47. Alternatively, the first and second channels 62 and 28 can extend into the bone-facing surface 47 of the links 40 along the transverse direction, but can terminate along the transverse direction without extending through the outer surface 48.

Figure 5A:
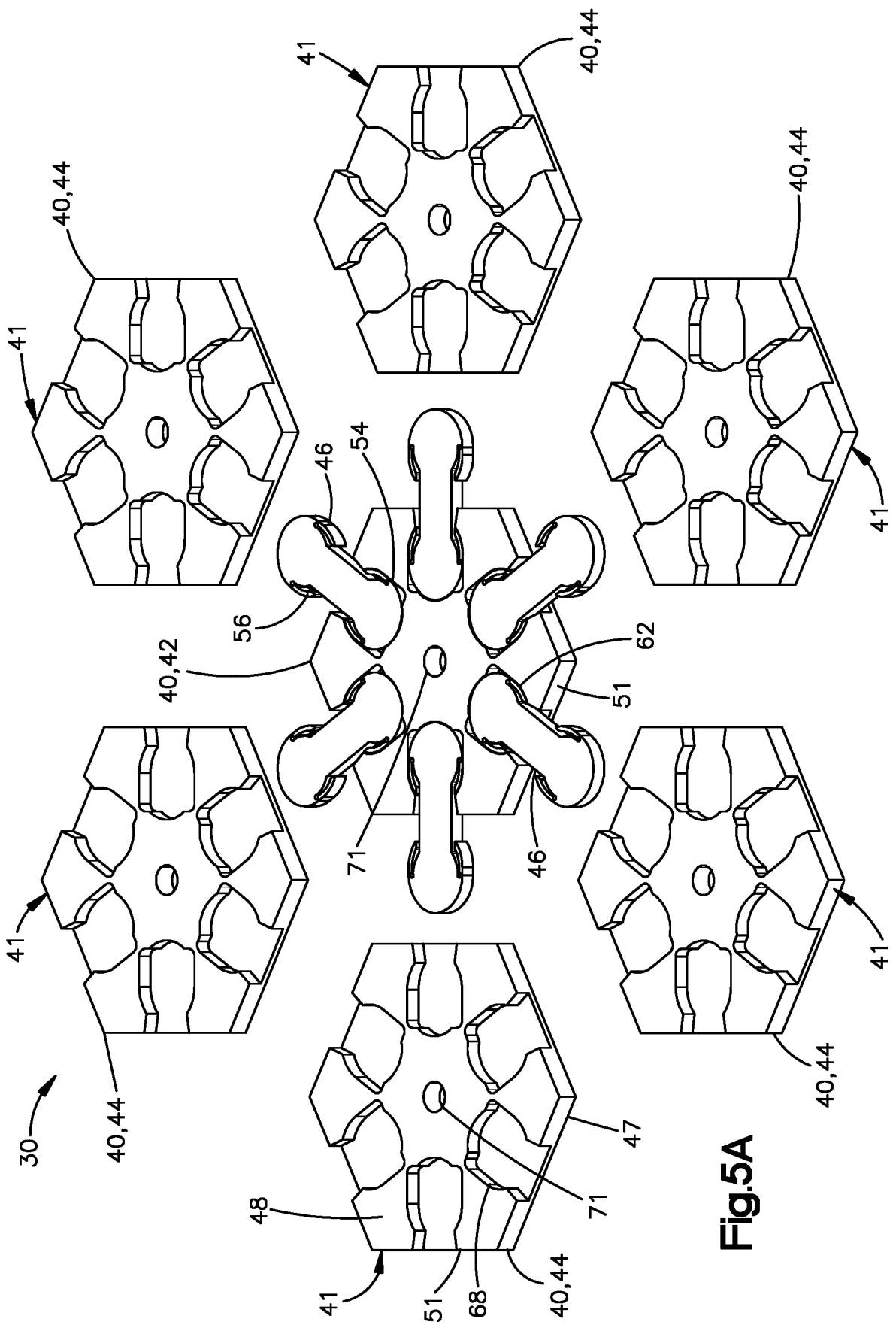
FIG. 5A is a perspective view of an expandable implant in yet another example, including a hub and a plurality of peripheral links.
Figure 5B:
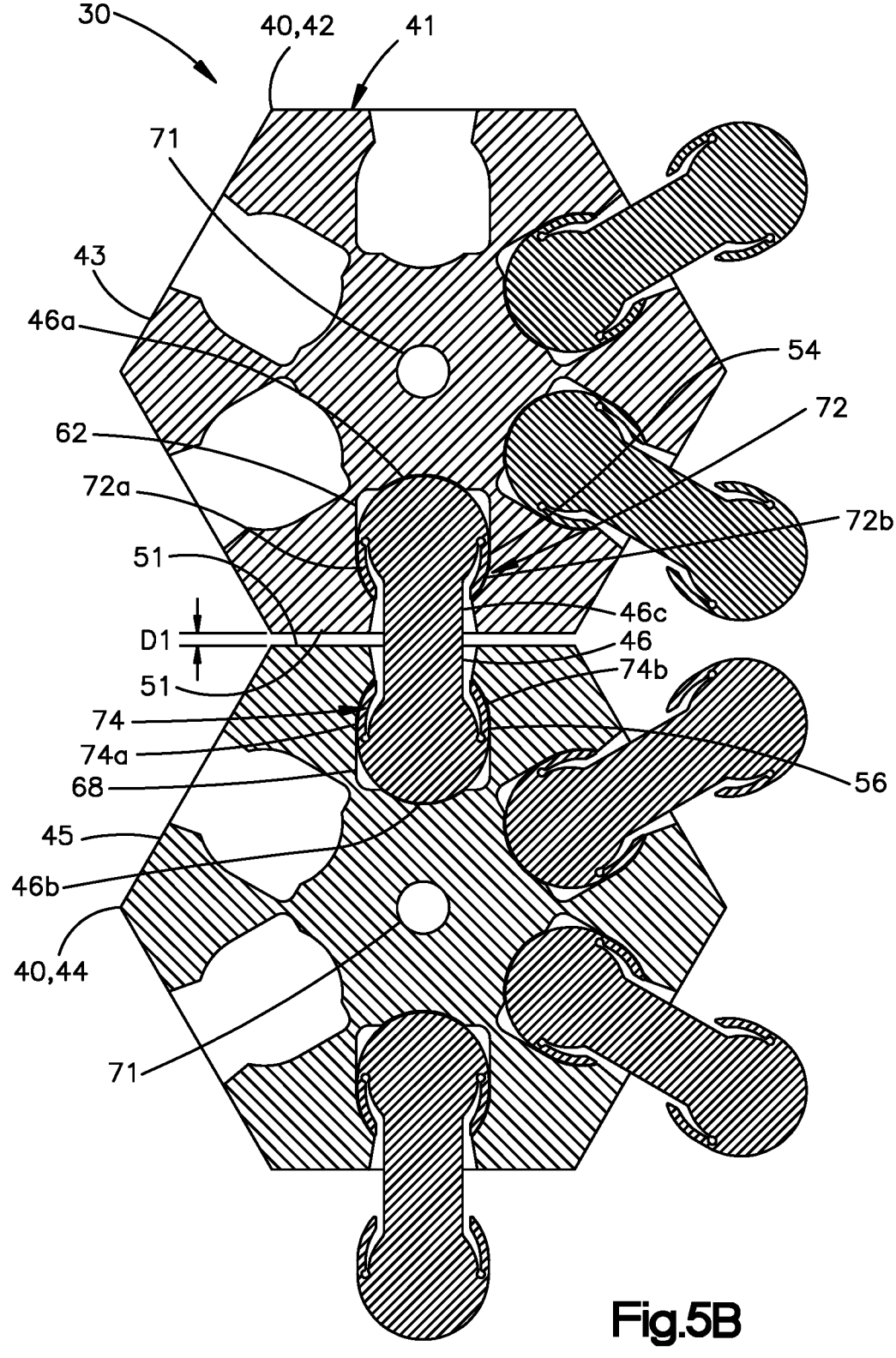
FIG. 5B is a perspective view of the hub and a peripheral link of the plurality of peripheral links of FIG. 5A, shown prior to expansion.
Figure 5C:
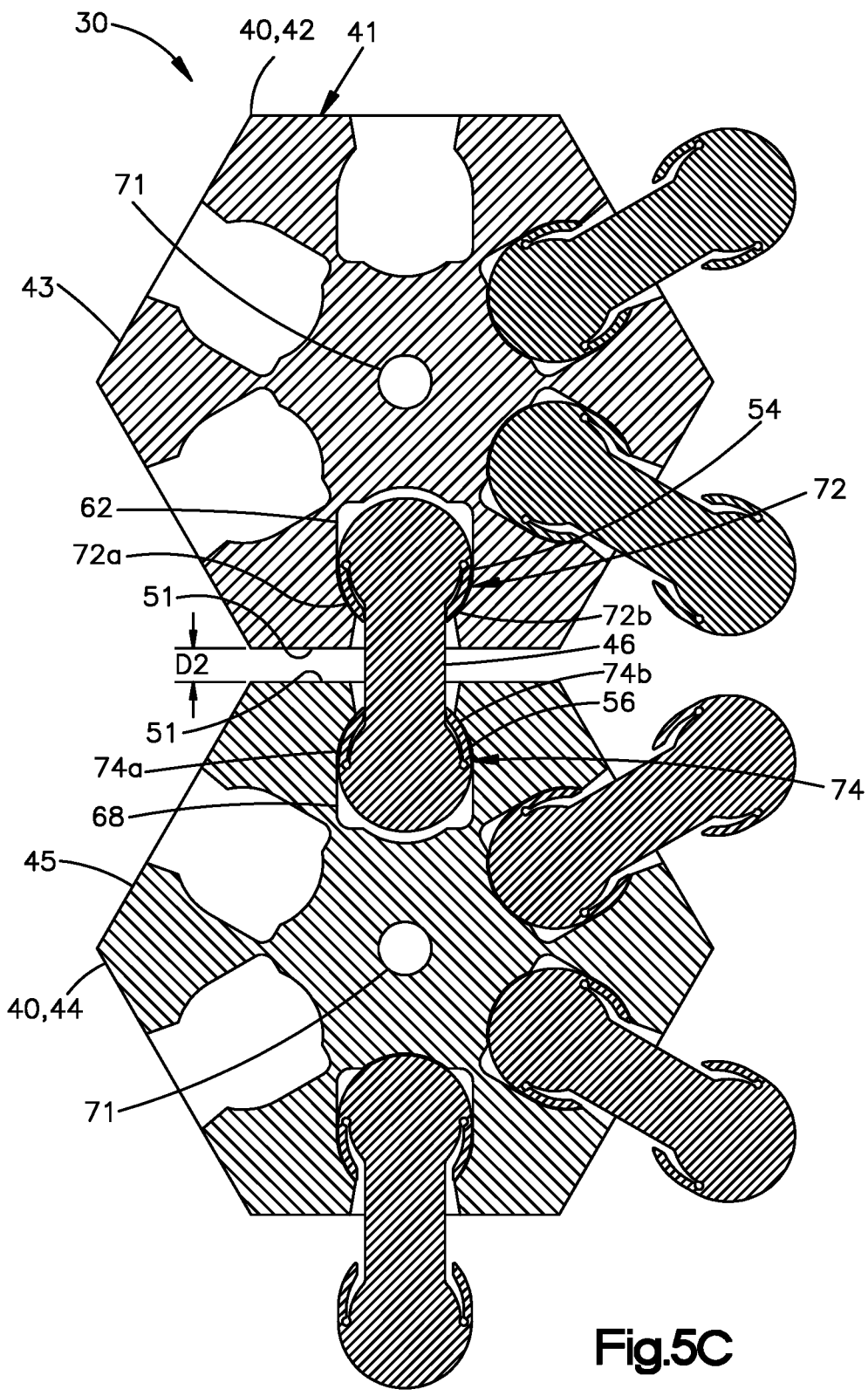
FIG. 5C is a perspective view of the hub and the peripheral link of FIG. 5B, shown after expansion.
Figure 6A:
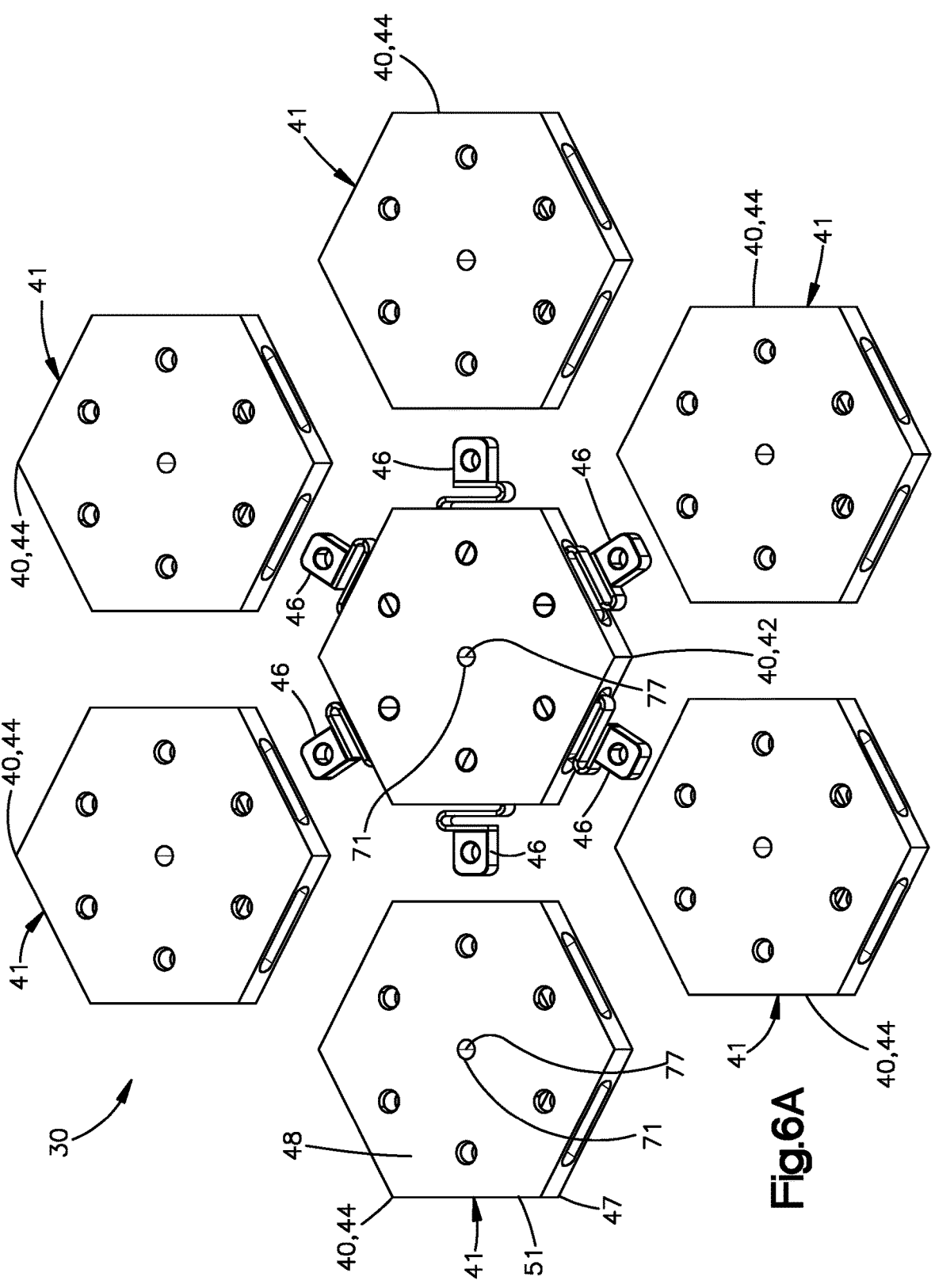
FIG. 6A is a perspective view of an expandable implant in still another example, including a hub and a plurality of peripheral links.
Figure 6B:
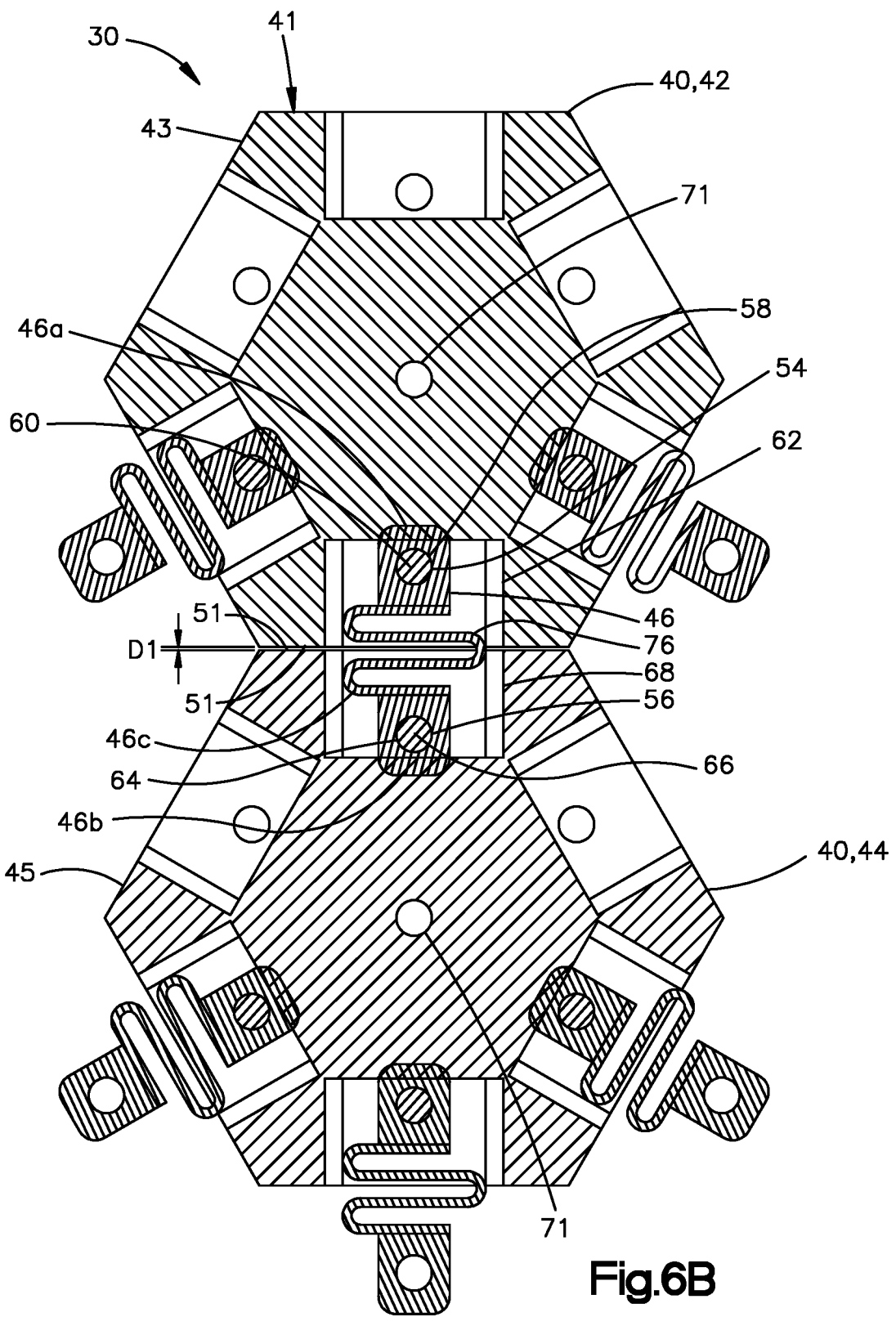
FIG. 6B is a perspective view of the hub and a peripheral link of the plurality of peripheral links of FIG. 6A, shown prior to expansion.
Figure 6C:
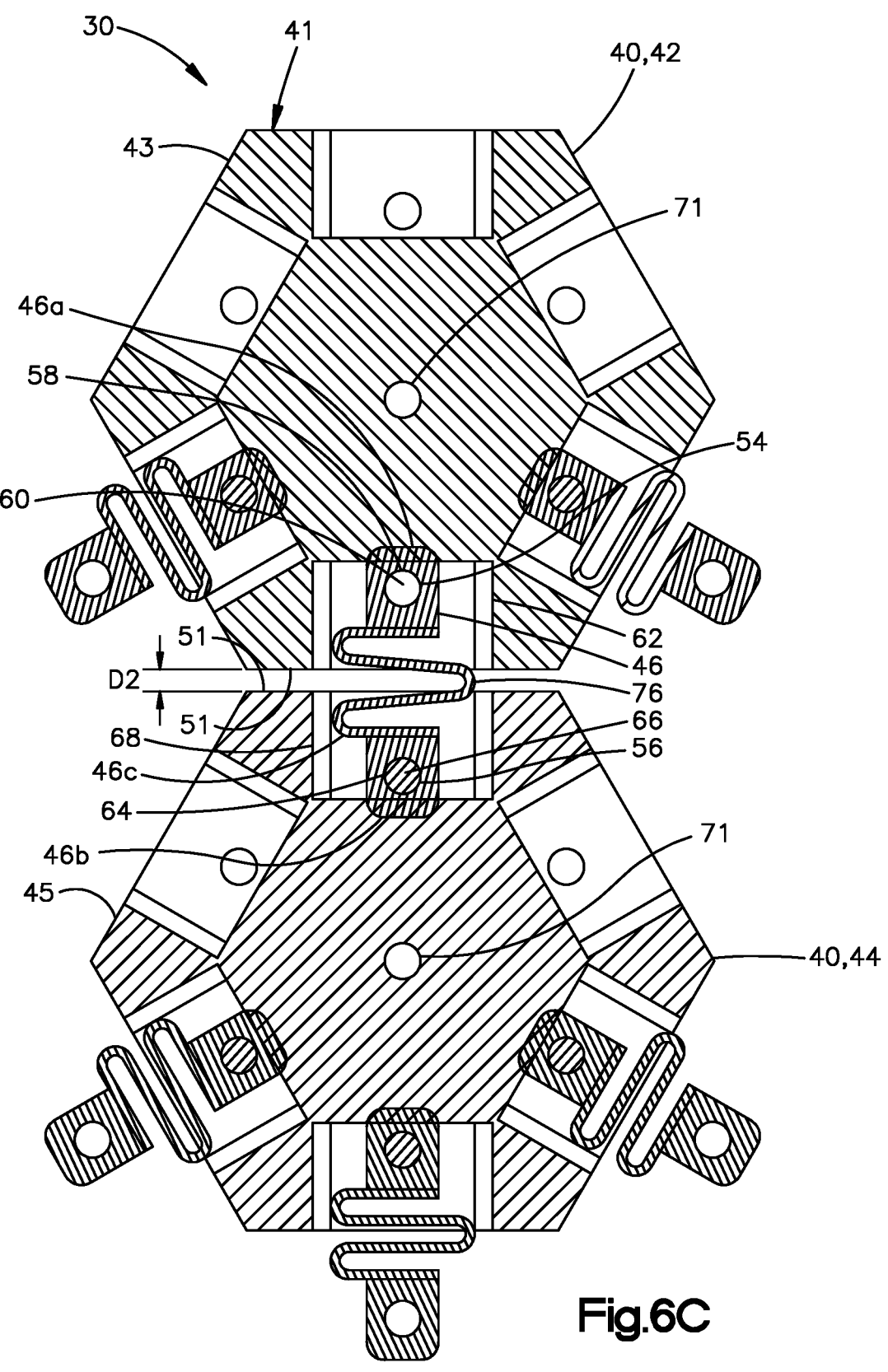
FIG. 6C is a perspective view of the hub and the peripheral link of FIG. 6B, shown after expansion.
Figures 7A, 7B:
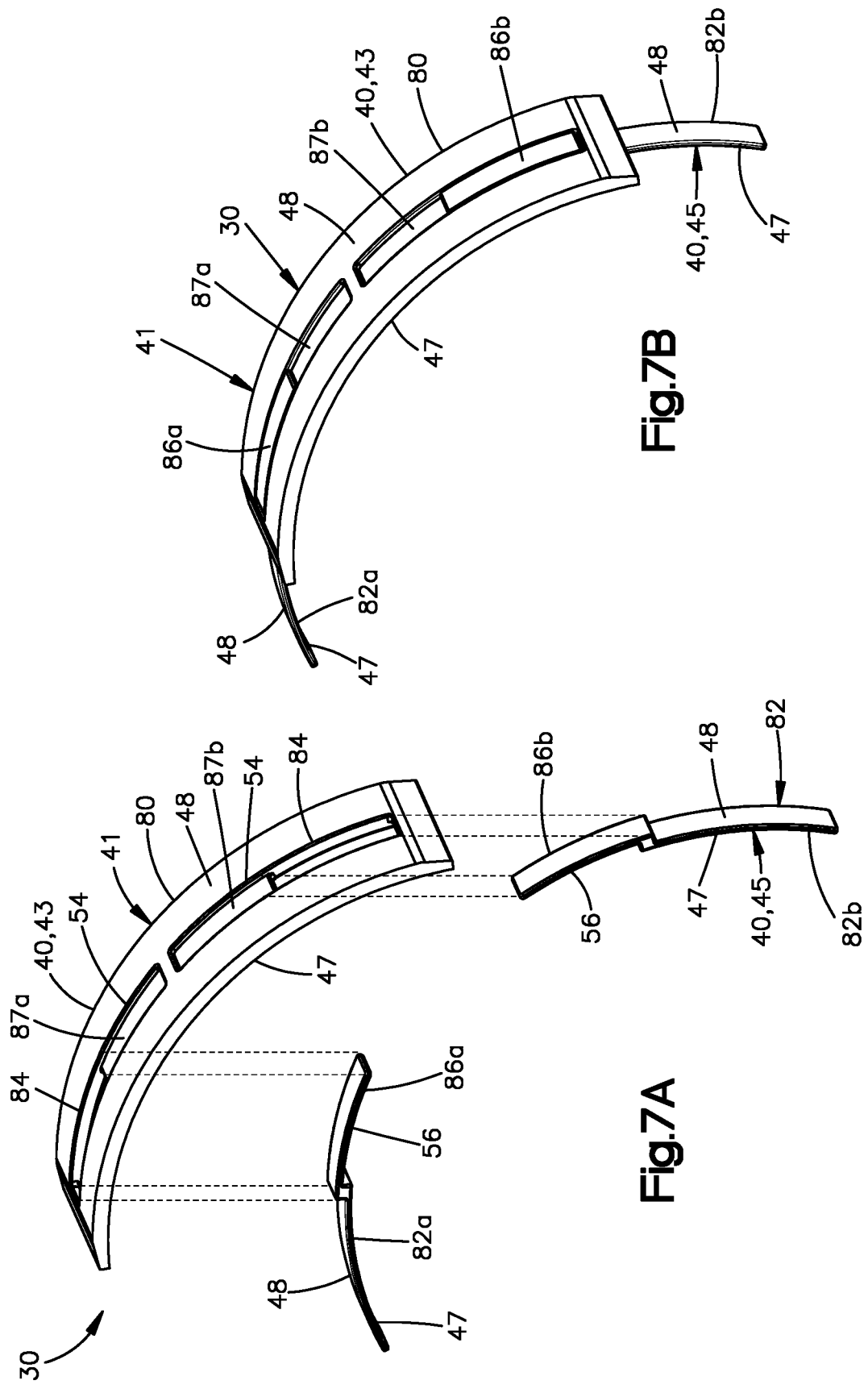
FIG. 7A is an exploded perspective view of an expandable implant in yet another example, including a first link and a second link including a plurality of tines that are translatable in the first link.
FIG. 7B is a perspective view of the expandable implant of FIG. 7A, shown prior to expansion in an unexpanded position.
Figures 7C, 7D:
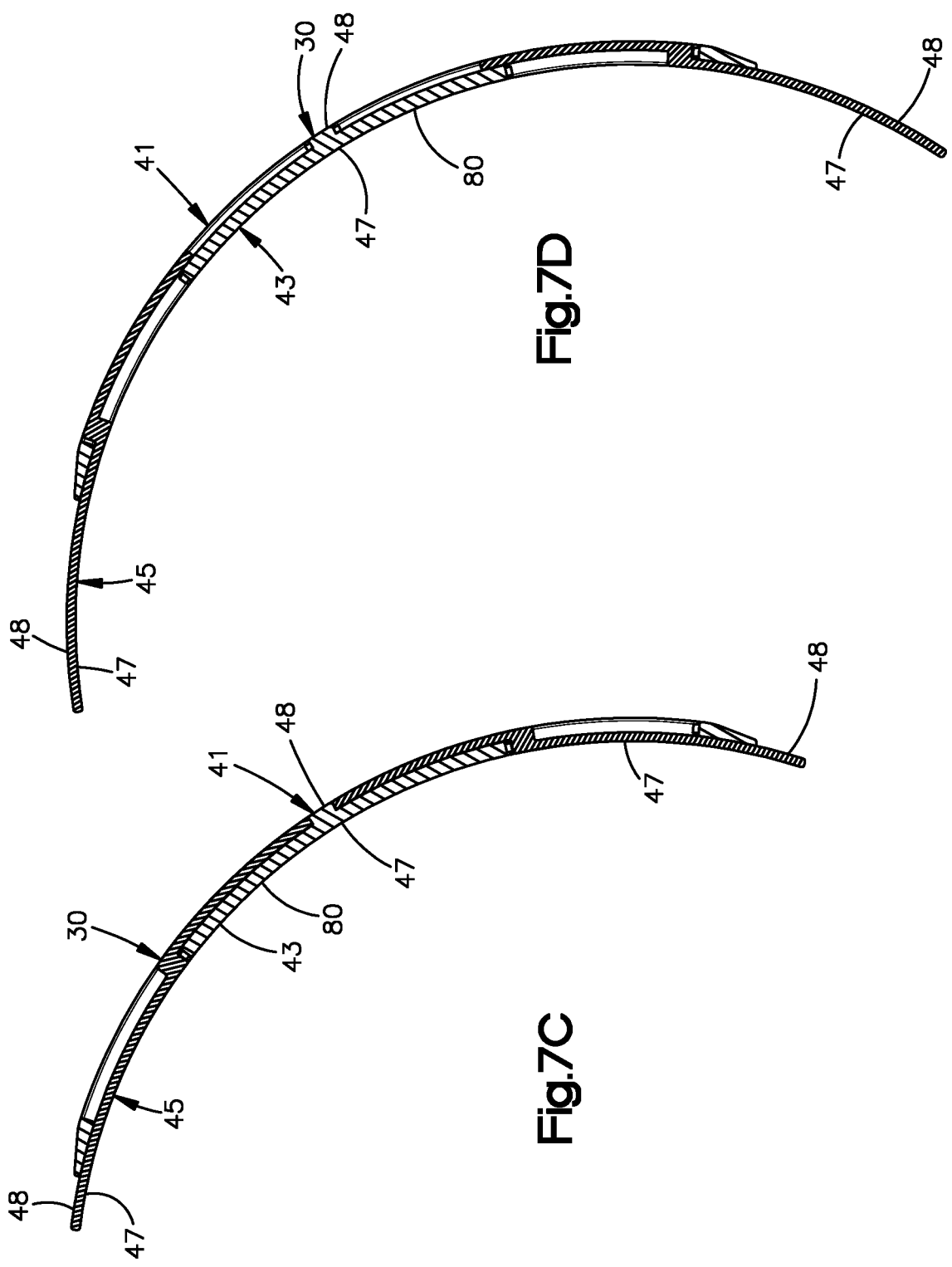
FIG. 7C is a side elevation view of the expandable implant of FIG. 7B, shown in the unexpanded position.
FIG. 7D is a side elevation view of the expandable implant of FIG. 7C, shown after expansion in an expanded position.

Accordingly, when the first and second retention arms 72a and 72b of the first pair 72 are resiliently compressible, the first and second retention arms 72a and 72b flex as they compress against the first link 43 as the first connection member 54 moves in the second direction of extension toward the second link 45 as illustrated at FIG. 5B. The compression of the first and second retention arms 72a and 72b can create clearance in the first channel 62 that permits the first connection member 54, and thus the connector 46, to translate in the second direction of extension, thereby allowing the first and second links 43 and 45 to move away from each other along the direction of expansion.

Similarly, when the first and second retention arms 74a and 74b of the second pair 74 are resiliently compressible, the first and second retention arms 74a and 74b flex as they compress against the second link 45 as the second connection member 56 moves in the first direction of extension toward the first link 43 as illustrated at FIG. 5B. The compression of the first and second retention arms 74a and 74b can create clearance in the second channel 68 that permits the second connection member 56, and thus the connector 46, to translate in the first direction of extension, thereby allowing the first and second links 43 and 45 to move away from each other along the direction of expansion. Thus, in some examples, the second connection member 56 can be devoid of an aperture 64 that receives a retention pin of the second link 45.

Referring now to FIGS. 2A-2D and 6A-6C, the connector 46 can be configured to permit movement of the first and second links 43 and 45 away from each other, in accordance with another example. In particular, the body 46c of the connector 46 can define a spring 76 that is disposed between the first and second connection members 54 and 56. The spring 76 can be monolithic with the body 46c so as to define a single unitary structure. Alternatively, the spring 76 can be separate from and attached to the connector 46. The spring 76 can be configured to flex as the first and second connection members 54 and 56 move away from each other along the direction of expansion. The first and second connection members 54 and 56 can be configured in accordance with any example as described above.

In one example, the first connection member 54 can define the first aperture 58 that is sized in cross-section substantially equal to the first retention pin 60 of the first link 43, such that the first retention pin 60 (and thus the first link 43) is substantially fixed with respect to translation relative to the connector 46 and thus relative to the second link 45. Similarly, the second connection member 56 can define the second aperture 64 that is sized in cross-section substantially equal to the second retention pin 66 of the second link 45, such that the second retention pin 66 (and thus the second link 45) is substantially fixed with respect to translation relative to the connector 46 and thus also relative to the first link 43. As a result, flexing of the spring 76 permits movement of the first and second links 43 and 45 with respect to each other along the direction of expansion. While the connectors 46 are shown having a discrete region that defines the spring 76 that can flex in the manner described above, it should be appreciated that the connectors 46 can be configured as a flexible member, such as a membrane, that can flex as described above, and thus defines the spring. In other examples, the connector 46 can define the spring, and either or both of the first connection members 54 and 56 can be translatably attached to the respective first and second links 43 and 45 in accordance with any example described herein.

Referring now to 2A-2D and FIGS. 7A-9B generally, it is recognized in further examples that can include at least one pair 41 of the first and second links 43 and 45. The first and second links 43 and 45 can be monolithic with the respective connector 46. Otherwise stated, the first link 43 can be monolithic with the first connection end 54, and the second link 45 can be monolithic with the second connection end 56. Thus, the first and second links 43 and 45 can be directly coupled to each other, such that the first and second links 43 and 45 are translatable away from each other along the respective direction of expansion. The first link 43 can include a first link body 80 that, as described above, can be curved or can be flexible such that the bone-facing surface 47 conforms to the underlying bone when the body 80 of the first link 43 is placed against the underlying cranium. The second link 45 can include a plurality of tines 82, such as first and second opposed tines 82a and 82b in one example. As described above, the tines 82 can be curved or can be flexible such that the bone-facing surface 47 conforms to the underlying bone when the tines 82 are placed against the underlying cranium.

As illustrated in FIGS. 7A-7D, the first link 43 can further include a first attachment member 54 that can be configured as an aperture 84 that extends through the first body 80 along the transverse direction. The aperture 84 can be continuous or segmented as desired. Further, the aperture 84 can be elongate along the direction of expansion. In this regard, the aperture 84 can be configured as at least one elongate slot 85. The second link 45 can include at least one first projection 86a that extends from the first tine 82a and is elongate along the direction of expansion. The first projection 86a can be jogged away from the first tine 82a in the transverse direction so as to extend into the aperture 84. Similarly, the second link 45 can include at least one second projection 86b that extends from the second tine 82b and is elongate along the direction of expansion. The first and second tines 82a and 82b can be oriented such that the first projection 86a extends from the first tine 82a toward the second projection 86b, and the second projection 86 extends from the second tine 82b toward the first projection 86a. The second projection 86b can be jogged away from the second tine 82b in the transverse direction so as to extend into the aperture 84. The second projection 86b can be translatably received in the aperture 84. In one example, the body 80 of the first link 40 can define first and second seats 87a and 87b that are disposed in the aperture and extends along a portion of the aperture that receives the projections 86a and 86b. The first and second projections 86a and 86b can translate along the respective first and second seats 87a and 87b as the respective first and second tines 82a and 82b as the projections 86a and 86b translated in the aperture 84. In another example, the first and second projections 86a and 86b and the aperture 84 can define a dovetail joint or any suitable alternative joint as desired that translatably couples the second tine 82b to the first link 43.

The first tine 82 can be fixed to the cranium at a first side of the cranial defect, the second tine 82 can be fixed to the cranium at an opposed second side of the cranial defect, and the first link 43 can span the cranial defect without attachment to the cranium. As the underlying cranium grows and expands, the first tine 82a can translate away from the second tine 82b in the elongate aperture 84 in a first direction of translation from an unexpanded position shown in FIG. 7C to an expanded position shown in FIG. 7D. Similarly, the second tine 82b can move or translate away from the first tine 82a in the elongate aperture 84 in a second direction of translation opposite the first direction of translation from the unexpanded position shown in FIG. 7C to the expanded position shown in FIG. 7D. As the first and second tines 82a and 82b move in the respective first and second directions of translation, the implant 30 thus expands from the unexpanded state to the expanded state. In this regard, the first and second directions of translation can be oriented along the direction of expansion. In some examples, the implant 30 can include a plurality of the pairs 41 first and second links 43 and 45 fixed to the underlying cranium as described herein. The first and second links 43 and 45 of the pairs 41 can be oriented parallel to each other in a common direction as desired, so as to expand in the common direction in response to expansion of the underlying cranium in the common direction. The pairs 41 can be separate from each other, or mechanically attached to each other as desired.

Figure 8B:
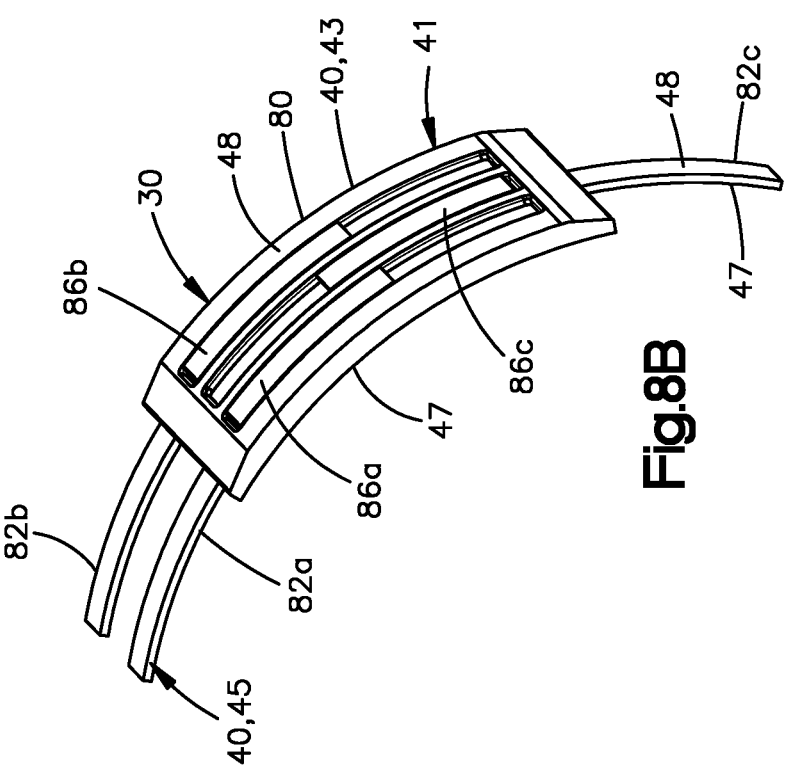
FIG. 8B is a perspective view of the expandable implant of FIG. 8A.
Figure 8A:
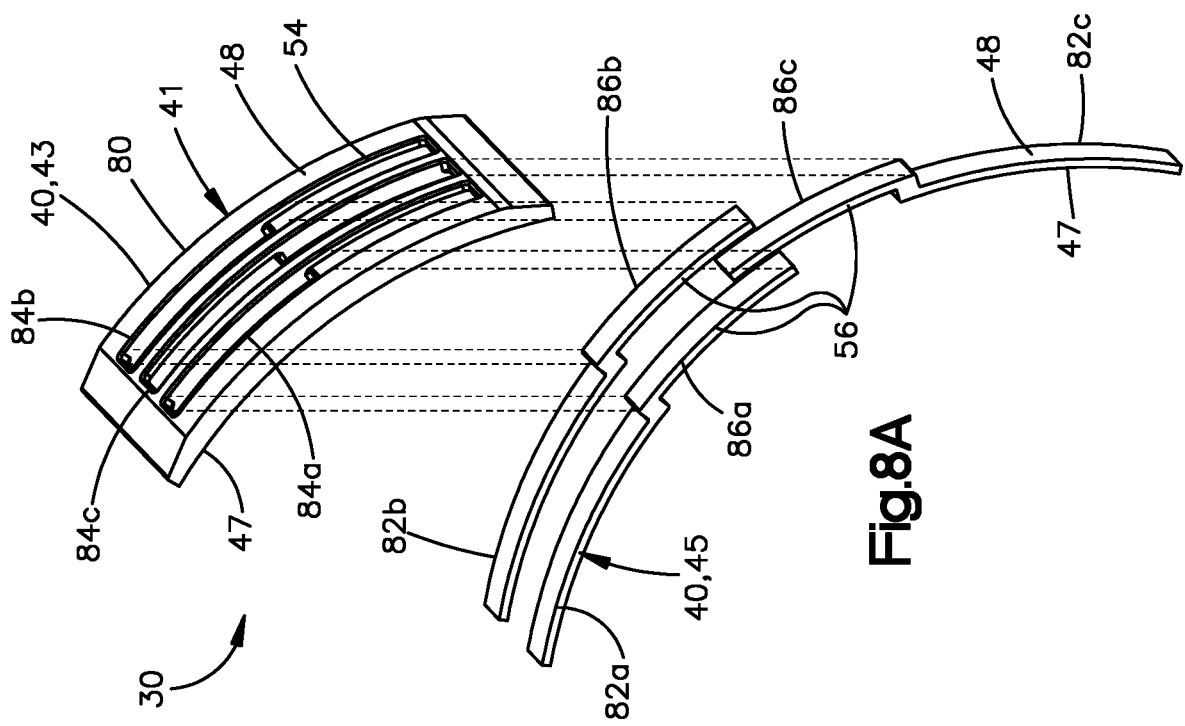
FIG. 8A is an exploded perspective view of an expandable implant in yet another example, including a first link and a second link including a plurality of tines that are translatable in the first link.

Referring to FIGS. 8A-8B, the first link 43 can include any number of apertures 84 as desired, each configured as a respective elongate slot 85. Similarly, the second link 45 can include any number of tines 82 as desired that are translatably received in the elongate slot 85. In one example, the first link 43 can define first, second, and third apertures 84a, 84b, and 84c that extend through the body 80 along the transverse direction. The apertures 84a-84c are disposed adjacent each other along a third direction that is oriented perpendicular to both the transverse direction and the direction of expansion. Further, the apertures 84a-84c can be aligned with each other along the third direction. In one example, the third aperture 84c can be disposed between the first and second apertures 84a and 84b with respect to the third direction.

The second link 45 can correspondingly include first, second, and third tines 82a, 82b, and 82c. The first and second tines 82a and 82b can be constructed and configured as described above to translate in the first direction of translation in the first and second apertures 84a and 84b, respectively. The second link 43 can include at least one third projection 86c that extends from the third tine 82c and is elongate along the direction of expansion. The third projection 86c can be jogged away from the third tine 82c in the transverse direction so as to extend into the aperture 84. The third projection 86c can be translatably received in the third aperture 84c. In one example, the third projection 86c and the third aperture 84c can define a dovetail joint or any suitable alternative joint as desired that translatably couples the third tine 82c to the first link 43.

As the underlying cranium grows and expands, the first and second tines 82a and 82b can translate in the first direction of translation as the respective first and second projections 86a and 86b translate in the respective first and second apertures 84a and 84b. The third tine 82c can move or translate in the second direction of translation opposite the first direction of translation, thereby expanding the implant 30. It should be appreciated that the first and second tines 82*a* and 82*b* can be included in a first group of at least one tine, such as a plurality of tines, that translate in the first direction of translation. Similarly, the third tine 82*c* can be included in a second group of at least one tine that translate in the second direction of translation. The first group of tines can be alternatingly arranged with the second group of at least one tine along the third direction. In this regard, the first group of tines and the second group of tines can include any number of tines as desired.

Figure 9B:
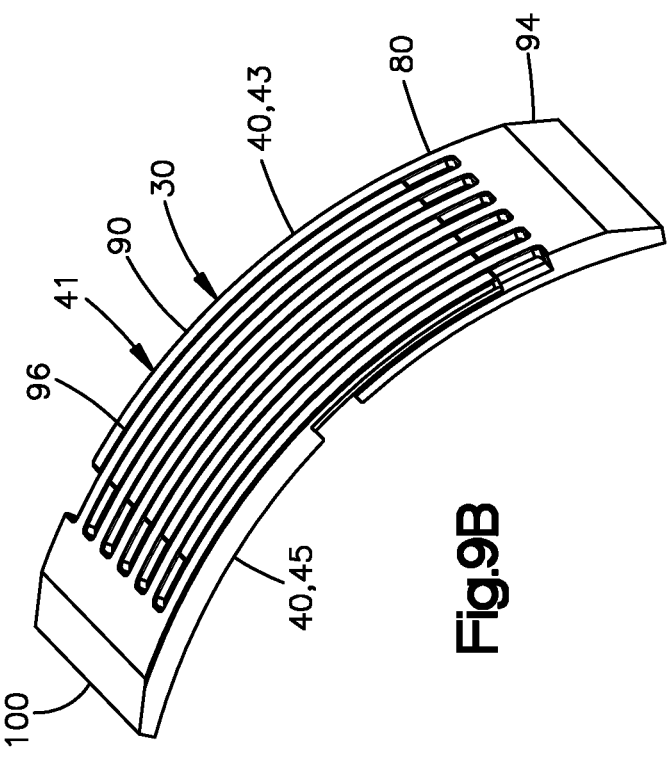
FIG. 9B is a perspective view of the expandable implant of FIG. 9A.
Figure 9A:
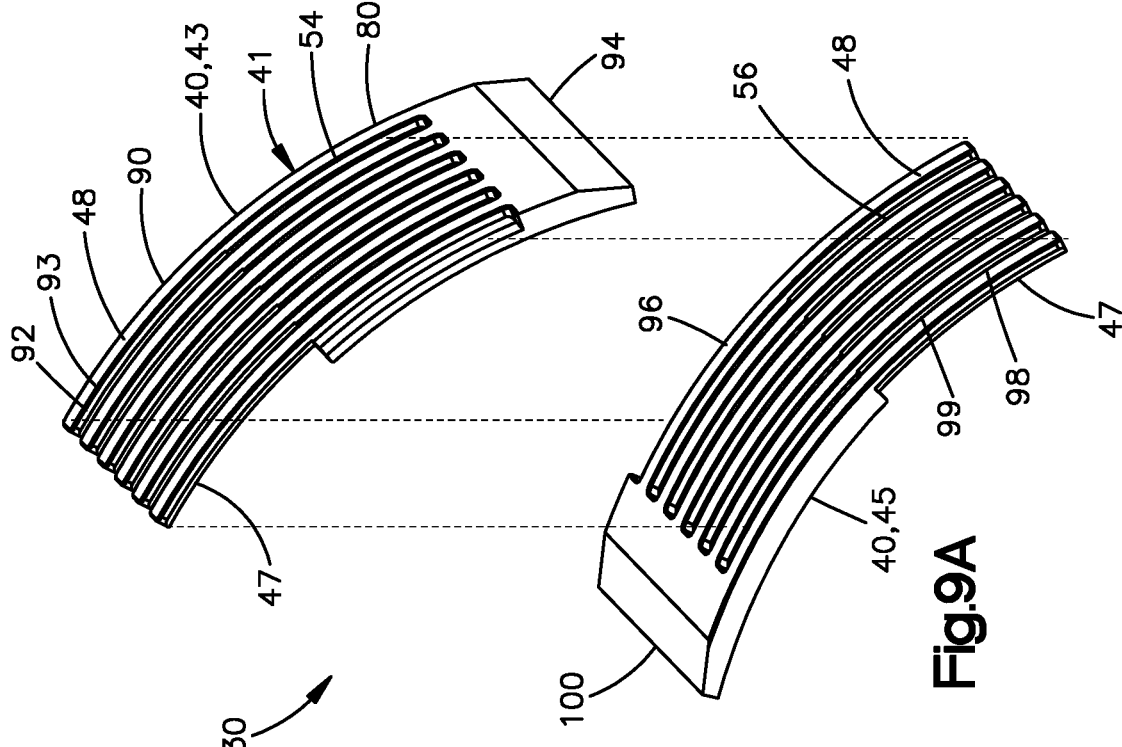
FIG. 9A is an exploded perspective view of an expandable implant in yet another example, including a first link including a first plurality of tines, and a second link including a second plurality of tines that are configured to translatably interdigitate with each other.

Referring now to FIGS. 9A-9B, it is recognized that each of the first and second links 43 and 45 can include respective first and second pluralities of interdigitating tines that are translatable with respect to each other along the direction of expansion. In particular, the first link 43 can include a plurality of first tines 90 that are spaced from each other along the third direction so as to define a plurality of first apertures 92 disposed between adjacent ones of the first tines 90. The first tines 90 and the first apertures 92 can be elongate along the direction of expansion. In this regard, the first apertures 92 can be referred to as first elongate slots 93. The first tines 90 can each be cantilevered from a common first base 94. The first base 94 can be monolithic with the first tines 90, or can be separate from the first tines 90 and attached to the first tines 90 as desired. The first base 94 can define one or more bone fixation holes (not shown) as desired that are configured to receive respective bone fixation members so as to fix the first link 43 to the underlying cranium at a first side of the cranial defect. The first tines 90 can be curved or can be flexible such that the bone-facing surface 47 conforms to the underlying bone when the first tines 90 are placed against the underlying cranium.

Similarly, the second link 43 can include a plurality of second tines 96 that are spaced from each other along the third direction so as to define a plurality of second apertures 98 disposed between adjacent ones of the second tines 96. The second tines 96 and the second apertures 98 can be elongate along the direction of expansion. The second apertures 98 can be therefore be referred to as second elongate slots 99. The second tines 96 can each be cantilevered from a common second base 100. The second base 100 can be monolithic with the second tines 96, or can be separate from the second tines 96 and attached to the second tines 96 as desired. The second base 100 can define one or more bone fixation holes (not shown) as desired that are configured to receive respective bone fixation members so as to fix the second link 45 to the underlying cranium at a second side of the cranial defect that is opposite the first side of the cranial defect. The second tines 96 can be curved or can be flexible such that the bone-facing surface 47 conforms to the underlying bone when the second tines 96 are placed against the underlying cranium.

The first apertures 92 can be sized to translatably receive respective ones of the plurality of second tines 96. Similarly, the second apertures 98 can be sized to translatably receive respective ones of the plurality of first tines 90. The first and second pluralities of tines 90 and 96 can be aligned with each other along the third direction, and oriented parallel to each other, along a common direction. As the underlying cranium grows and expands along the common direction, the first tines 90 can translate in the second apertures 90 in the first direction of translation, and the second tines 96 can translate in the first apertures 92 in the second direction of translation opposite the first direction of translation, thereby expanding the implant 30. In some examples, the implant 30 can include a plurality of the pairs 41 first and second links 43 and 45 fixed to the underlying cranium as described herein.

It should be appreciated that methods of attaching the implant 30 in accordance with any example described herein can include the steps of placing the implant against an underlying bone, such as the cranium or the skull, such that the implant extends across a bone defect of the skull, and attaching the implant to the skull on opposite sides of the bone defect at respective attachment locations. The method can further include the step of causing the implant 30 to expand from a first size to a second size due to expansion of the skull between the attachment locations. The implant 30 can include first and second links 43 and 45 in any example described herein. It should be appreciated that the implant 30 has been described as a cranial implant that is configured to be fixed to an underlying cranium so as to promote healing of a cranial defect, it is recognized that the implant 30 can be configured as any suitable implant as desired that is configured to fixed to any suitable underlying anatomical structure, such as any suitable underlying bone. The implant 30 can have particular advantages when fixed to an underlying bone that grows and expands over time.

It will be understood by those having ordinary skill in the art that various manufacturing methods may be used to manufacture the implants 30 and components thereof as described herein. For instance, the implants 30 and components thereof can be fabricated using additive manufacturing, such as 3D printing. When the implants 30 and their components are 3D printed, the implants 30 and their components can be 3D printed from at least one material such as multiple materials. For instance, in one example, at least one material can be defined by a biological substance. The 3D printing process can further be configured as a 4D printing process, wherein the implants 30 and components thereof can be printed in a flat configuration, and subsequently manipulated into the desired shape using origami techniques. In other examples, the implants 30 and components thereof can be fabricated using subtractive manufacturing, such as milling and assembling. In other examples, the implants 30 and components thereof can be manufactured using both additive and subtractive manufacturing techniques. In the alternative, the implants 30 and components thereof can be injection molded or stamped and cut from a flat sheet and formed to the anatomical shape either during manufacture or in a clinic on an anatomical model. In other examples, the pre-designed implants and components thereof, including the links 40, can be shaped by the user to fit the underlying bone. In still other examples, the pre-designed implants and components therefore, such as the links 40, can be trimmed by the user to the near net shape of the patient.

In yet another embodiment, the implants and components thereof can be pre-designed as patient-specific in the manner described above. In particular, the implants can be fabricated according to a surgical plan. In this process, a clinician or engineer can use DICOM® (Digital Imaging and Communications in Medicine) data of a patient to create a 3D implant design using digital, semi-automated software. Points could be placed along the surface of a filled defect (or splines that create the desired shape); the links can then be positioned on those points, with the bone facing surface of the links oriented normal to the surface of the bone. The external surfaces of the assembly are shaped to follow the patient anatomical skull.

It should be appreciated that the illustrations and discussions of the examples shown in the figures are for exemplary purposes only, and should not be construed limiting the disclosure. One skilled in the art will appreciate that the present disclosure contemplates various examples. Additionally, it should be understood that the concepts described above with the above-described examples may be employed alone or in combination with any of the other examples described above. It should be further appreciated that the various alternative examples described above with respect to one illustrated examples can apply to all examples as described herein, unless otherwise indicated.

What is claimed:

1. An expandable bone implant comprising:

a plurality of interconnected links including a hub and a plurality of peripheral links, wherein at least two of the interconnected links define respective bone fixation holes that are configured to receive respective bone fixation elements so as to fix the implant to an underlying bone; and a plurality of connectors connected to the hub and respective different ones of the plurality of peripheral links, such that the peripheral links are spaced from the hub in a medial-lateral direction and an anterior-posterior direction, wherein the connectors are elongate from the hub to the respective different ones of the plurality of peripheral links along respective directions of extension;

wherein the interconnected links are configured such that when the implant is fixed to the underlying bone, growth of the underlying bone causes the connectors to expand the implant from a first size to a second size, wherein the hub and at least some of the plurality of peripheral links are spaced apart from each other by respective first distances or abut each other along the respective directions of extension at the first size, and the at least some of the plurality of peripheral links are movable away from the hub to the second size along the respective directions of extension more than respective perpendicular directions that are perpendicular to the respective directions of extension, such that the at least some of the plurality of peripheral links are spaced from the hub at respective second distances along the respective directions of extension, and wherein the connectors are translatably coupled to at least one of the hub and the respective different one of the peripheral links so as to permit movement of the peripheral links away from the hub in a straight linear direction.

2. An expandable bone implant comprising:

a plurality of interconnected links including a hub and a plurality of peripheral links, wherein at least two of the interconnected links define respective bone fixation holes that are configured to receive respective bone fixation elements so as to fix the implant to an underlying bone; and a plurality of connectors connected to the hub and respective different ones of the plurality of peripheral links, such that the peripheral links are spaced from the hub in a medial-lateral direction and an anterior-posterior direction, wherein the connectors are elongate from the hub to the respective different ones of the plurality of peripheral links along respective directions of extension;

wherein the interconnected links are configured such that when the implant is fixed to the underlying bone, growth of the underlying bone causes the connectors to expand the implant from a first size to a second size, wherein the hub and at least some of the plurality of peripheral links are spaced apart from each other by respective first distances or abut each other along the respective directions of extension at the first size, and the at least some of the plurality of peripheral links are movable away from the hub to the second size along the respective directions of extension more than respective perpendicular directions that are perpendicular to the respective directions of extension, such that the at least some of the plurality of peripheral links are spaced from the hub at respective second distances along the respective directions of extension, and wherein the hub and the peripheral links define respective channels, and the connectors define first and second opposed connection members that are received in respective channels of the hub and a respective different one of the peripheral links.

3. The expandable bone implant of claim 2, wherein the connectors are movable in at least one of the channels as the implant expands from the first size to the second size.

4. The expandable bone implant of claim 2, wherein the first and second connection members comprise retention arms that bear against the interconnected links in the respective channels so as to capture the connectors therein.

5. The expandable bone implant of claim 2, wherein at least one of the first and second connection members comprises a slot that slidably receives a retention pin of one of the hub and the respective different one of the peripheral links.

6. The expandable bone implant of claim 5, wherein the other of the first and second connection members is translationally fixed to the other of the hub and the respective different one of the peripheral links.

7. The expandable bone implant of claim 6, wherein the other of the first and second connection members comprises an aperture opposite the slot, the aperture sized to receive a retention pin of the other of the hub and the respective different one of the peripheral links, thereby translationally fixing the connectors to the other of the hub and the respective different one of the peripheral links.

8. The expandable bone implant of claim 6, wherein the other of the first and second connection members is press fit in a channel the other of the hub and the respective different one of the peripheral links so as to translationally fix the connectors to the other of the hub and the respective different one of the peripheral links.

9. The expandable bone implant of claim 2, wherein at least one of the first and second connection members comprises resilient retention arms that bear against the interconnected links in the respective channels so as to capture the connectors therein, and the arms flex as the connector moves with respect to the at least one of the hub and the respective different one of the peripheral links.

10. The expandable bone implant of claim 2, wherein the connectors define a spring disposed between the first and second connection members, the spring configured to flex as the respective adjacent ones of the plurality of interconnected links move away from each other as the implant expands from the first size to the second size.

* * * * *